(12) United States Patent
Lippert

(10) Patent No.: US 9,848,882 B2
(45) Date of Patent: Dec. 26, 2017

(54) MICRO-FABRICATED EMBOLIC DEVICES

(71) Applicant: Scientia Vascular, LLC, West Valley City, UT (US)

(72) Inventor: John Lippert, Incline Village, NV (US)

(73) Assignee: Scientia Vascular, LLC, Salt Lake City, UT (US)

( * ) Notice: Subject to any disclaimer, the term of this patent is extended or adjusted under 35 U.S.C. 154(b) by 578 days.

(21) Appl. No.: 14/199,675

(22) Filed: Mar. 6, 2014

(65) Prior Publication Data

US 2014/0257363 A1 Sep. 11, 2014

Related U.S. Application Data

(60) Provisional application No. 61/775,433, filed on Mar. 8, 2013.

(51) Int. Cl.
*A61B 17/12* (2006.01)
*A61B 17/00* (2006.01)

(52) U.S. Cl.
CPC .... *A61B 17/12113* (2013.01); *A61B 17/1214* (2013.01); *A61B 17/12022* (2013.01);
(Continued)

(58) Field of Classification Search
CPC ........ A61B 17/12027; A61B 17/12031; A61B 17/12036; A61B 17/1204;
(Continued)

(56) References Cited

U.S. PATENT DOCUMENTS 5,102,390 A 4/1992 Crittenden et al.
5,326,374 A 7/1994 Ilbawi et al.
(Continued)

FOREIGN PATENT DOCUMENTS

| AU | 2008229892 | 10/2008 |
|---|---|---|
| WO | 94/06503 | 3/1994 |
| WO | 2014138580 | 9/2014 |

OTHER PUBLICATIONS

International Search Report and Written Opinion for PCT/US14/21742 dated Aug. 27, 2014.
(Continued)

*Primary Examiner* — Ryan J Severson
*Assistant Examiner* — Christian Knauss
(74) *Attorney, Agent, or Firm* — Workman Nydegger

(57) ABSTRACT

An embodiment is directed to an embolic device comprised of a coil made of a first material and disposed on the inside of a tube structure made of a second material. The tube structure has micro-fabricated fenestrations formed in the tube to provide fluid communication between the lumen of the tube and the surrounding environment, thereby exposing the inner coil. The fenestrations also trip flow around the embolic device. In one embodiment, the embolic device is comprised of a tantalum coil on the inside of a polyetheretherketone (PEEK) tube. The PEEK tube has the advantage of providing a micro-machined delivery implant frame and radiopacity, while the internal tantalum coil provides radiopacity and thrombogenicity. A material other than PEEK may be used for embodiments of embolic devices without departing from the spirit of the disclosure.

15 Claims, 26 Drawing Sheets

(52) U.S. Cl.
CPC ............... *A61B 17/12031* (2013.01); *A61B 2017/00309* (2013.01); *A61B 2017/00526* (2013.01); *A61B 2017/00831* (2013.01); *A61B 2017/00884* (2013.01); *A61B 2017/1205* (2013.01); *A61B 2017/12054* (2013.01)

(58) Field of Classification Search
CPC ........ A61B 17/12099; A61B 17/12109; A61B 17/12113; A61B 17/1214; A61B 17/12145; A61B 17/1215; A61B 17/12168; A61B 17/12172; A61B 17/12177; A61F 2/91; A61F 2002/823; A61F 2002/826
See application file for complete search history.

(56) References Cited

U.S. PATENT DOCUMENTS

| | | | | |
|---|---|---|---|---|
| 5,382,259 | A * | 1/1995 | Phelps | A61B 17/12022 604/907 |
| 5,554,114 | A * | 9/1996 | Wallace | A61B 17/22 604/508 |
| 5,792,154 | A * | 8/1998 | Doan | A61B 17/12022 128/831 |
| 6,168,570 | B1 * | 1/2001 | Ferrera | A61B 17/12022 600/585 |
| 6,183,410 | B1 * | 2/2001 | Jacobsen | A61N 5/1002 600/3 |
| 6,440,088 | B1 | 8/2002 | Jacobsen et al. | |
| 8,377,056 | B2 | 2/2013 | Oyola et al. | |
| 8,468,919 | B2 | 6/2013 | Christian et al. | |
| 2004/0186485 | A1 * | 9/2004 | Kear | A61B 17/221 606/127 |
| 2005/0274384 | A1 | 12/2005 | Tran et al. | |
| 2006/0041186 | A1 | 2/2006 | Vancaillie | |
| 2007/0142893 | A1 | 6/2007 | Buiser et al. | |
| 2007/0221230 | A1 * | 9/2007 | Thompson | A61B 17/12022 128/207.15 |
| 2008/0086854 | A1 * | 4/2008 | Boyd | A61B 17/064 24/715.3 |
| 2008/0119869 | A1 | 5/2008 | Teague et al. | |
| 2008/0319525 | A1 * | 12/2008 | Tieu | A61F 2/86 623/1.11 |
| 2009/0036833 | A1 * | 2/2009 | Parins | A61M 25/00 604/164.13 |
| 2009/0043283 | A1 | 2/2009 | Turnlund et al. | |
| 2010/0114017 | A1 | 5/2010 | Lenker et al. | |
| 2010/0114302 | A1 | 5/2010 | Tzafriri et al. | |
| 2010/0256606 | A1 | 10/2010 | Lippert et al. | |
| 2011/0022003 | A1 | 1/2011 | Tekulve | |
| 2012/0158034 | A1 | 6/2012 | Wilson et al. | |
| 2012/0239074 | A1 * | 9/2012 | Aboytes | A61B 17/12113 606/191 |
| 2012/0271397 | A1 | 10/2012 | Muzslay et al. | |
| 2013/0018359 | A1 | 1/2013 | Coyle | |

OTHER PUBLICATIONS

Supplementary Partial European Search Report for EP14760849 dated Oct. 11, 2016.

* cited by examiner

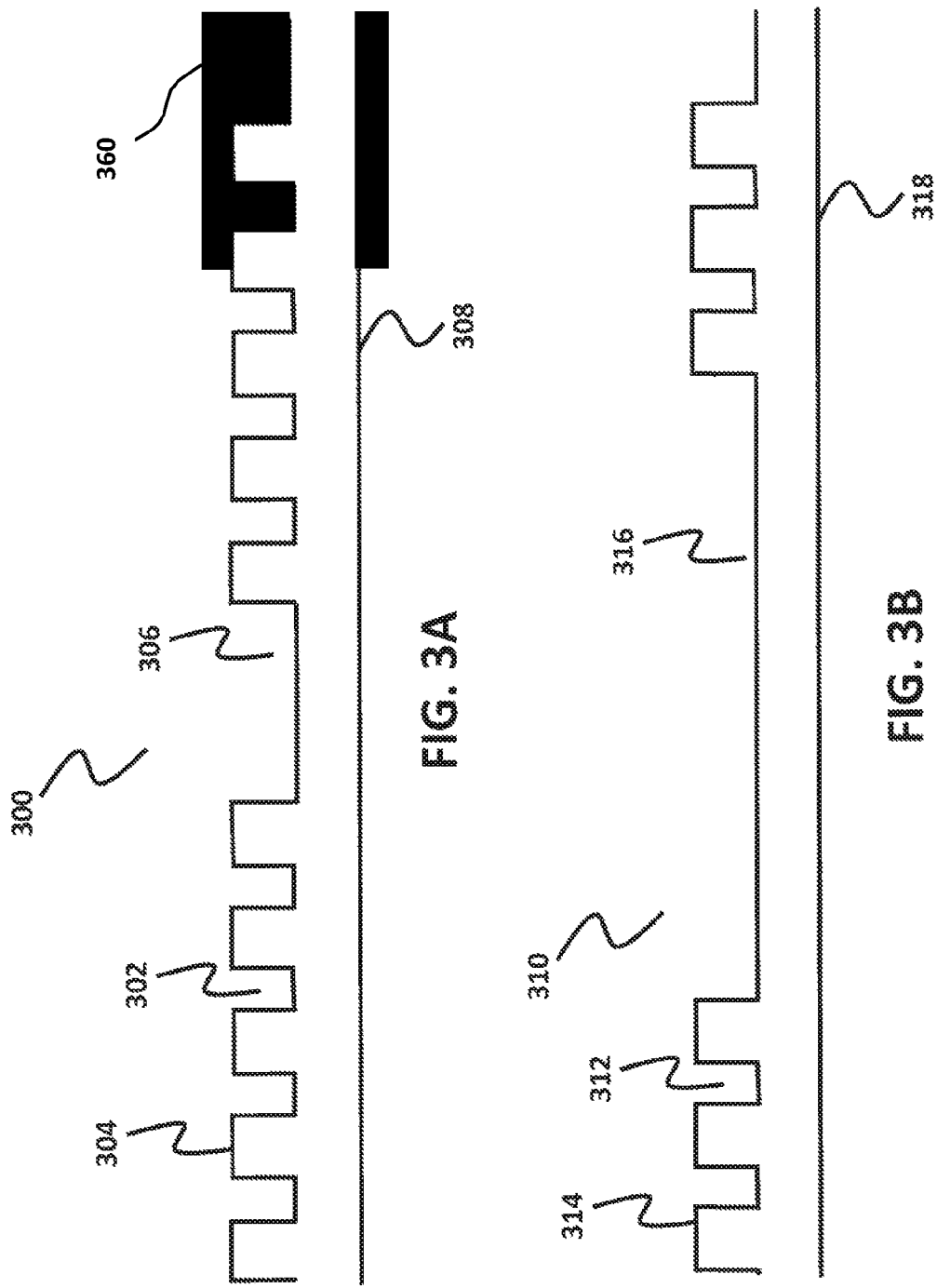

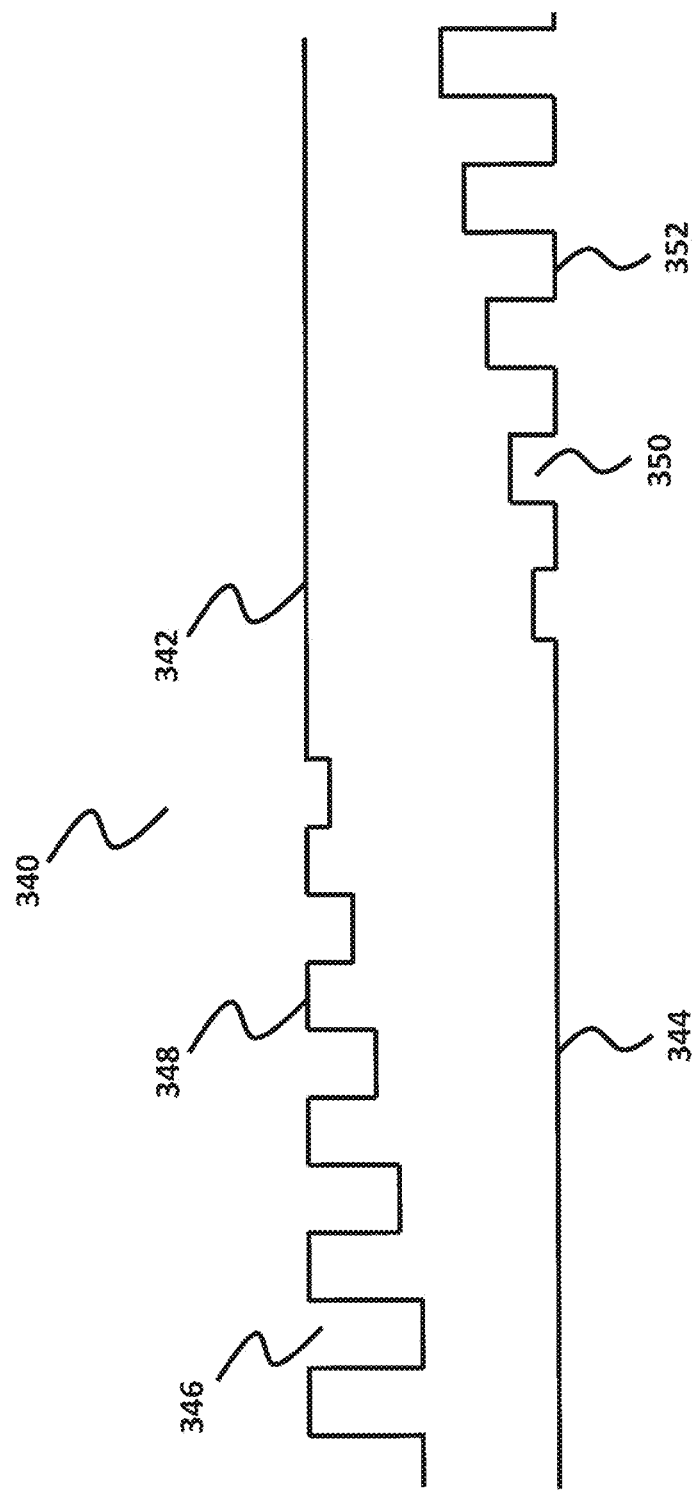

MICRO-FABRICATED EMBOLIC DEVICES

CROSS-REFERENCE TO RELATED APPLICATIONS

This application claims priority to, and the benefit of, U.S. Provisional Patent Application Ser. No. 61/775,433, filed on Mar. 8, 2013, and entitled "MICRO-FABRICATED EMBOLIC DEVICES," the entirety of which is incorporated herein by reference.

BACKGROUND

The medical field utilizes highly flexible and torqueable catheters and guidewires to perform delicate procedures deep inside the human body. Endovascular procedures typically start at the groin where a catheter and/or guidewire are inserted into the femoral artery and navigated up to the heart, brain, or other anatomy as required. Once in place, the guidewire is removed so the catheter may be used for the delivery of drugs, stents, embolic devices, or other devices or agents. The catheter may be a balloon catheter used for therapy directly, either by itself or with a balloon expandable stent pre-loaded on it. A radiopaque dye is often injected into the catheter so that the vessels may be viewed intraprocedurally or in the case of a diagnostic procedure, the dye may be the primary or only agent delivered through the catheter.

Intravascular procedures, by definition, work in and with delicate anatomy, namely the vessels themselves, which are often also compromised by disease. Damage to the vessels is particularly critical to avoid. If blood in the vessels is allowed to "leak," direct damage may be caused to any tissue outside of the normal capillary approach contacted by the blood, and/or may result in a deadly problem of exsanguination or "bleed out". When treating an aneurysm, the control of the catheter tip is especially important. An aneurysm is a very fragile ballooned vessel wall which can easily be punctured if the guidewire or catheter is not precisely controlled.

Embolic coils are typically wound from fine platinum wire into a primary diameter sized for delivery through standard catheters. Standard catheters typically have a diameter of 0.014 inches to 0.035 inches, while embolic coils are typically wound to a 0.002 inch or 0.003 inch diameter. The coils are cut to length and a secondary shape or helix is set into the coil. The embolic coil is a device that can fill an anatomical structure. Embolic coils are usually used to fill or partially assume the shape and size of a vessel, an aneurysm, a fistula, etc. When the coil is inserted through a catheter and released into the body, the coil structure can slow or arrest blood flow, providing a surface for platelet aggregation and clot formation.

Advances in embolic coils include the addition of Dacron or polyester fibers, the addition of hydrophilic polymers, and the use of alternative shapes to standard cylindrical or helical primary coils. These advances have been designed in response to desires for improved and faster clotting (increased thrombogenicity through increased surface area) and/or blood flow arrest, better filling and/or holding force (interconnection), and greater filling density through swelling polymer post coil placement. However, these advances have not yielded demonstrable clinical benefit. In the case of the hydrophilic swelling polymer, potential negative clinical issues have manifested all the while clinical use increases. Furthermore, any perceived benefit from increased filling density from hydrophilic polymers is offset by the understanding that a water bearing surface is likely to be the least integrated into living tissue. That is, the "wet ball" surface is both geometrically and chemically the least optimal for tissue in-growth, integration, and stability.

Typically coils are made of a solid wire coil, which is wound in a "stacked" configuration, i.e. each subsequent adjoining coil strand is placed or added without any gap between the wire strands. This limits the ways in which the embolic coil may be shaped and its thrombogenic properties, among other limitations. The use of platinum embolic coils typically requires a large number of coils to occlude a volume, as platinum embolic coils do not have a high thrombogenicity. The platinum coils also tend to pack (i.e. compress in situ), reducing the effective filling of the aneurysm. This increases the risk of the aneurysm rupturing, a recurrence of the aneurysm, or another aneurysm forming near the occluded aneurysm. As such, it would be desirable to have improved embolic coils.

SUMMARY

An embodiment is directed to an embolic device comprised of a micro-fabricated tube having an outer surface and an inner surface. The inner surface forms a lumen extending form a proximal end to a distal end. The tube is made of a first material and has one or more micro-fabricated fenestrations formed from the outer surface the tube to the lumen. The embolic device also includes an inner coil made of a second material and disposed on the inside of the tube. The one or more fenestrations formed in the tube expose the inner coil. In another embodiment, the embolic device is comprised of a tantalum coil on the inside of a polyetheretherketone (PEEK) tube. PEEK may also be combined with other types of polymers, such as polyether block amide (PEBA), carbon fibers, and glass fibers.

In yet another embodiment, an embolic device comprises a micro-fabricated tube having an outer surface and an inner surface. The inner surface forms a lumen extending form a proximal end to a distal end. The tube is made of a first material and has one or more micro-fabricated fenestrations formed from the outer surface the tube to the lumen. The embolic device also includes an inner coil made of a second material and disposed on the inside of the tube. The one or more fenestrations formed in the tube expose the inner coil. The embolic device also has a preferred deployed state when deployed. The fenestrations formed in the tube are selected to provide a preferred orientation of bending when the embolic device is deployed.

In a further embodiment, a method of packaging an embolic device comprising a tube and an inner coil disposed within the tube is presented. The method includes packaging and sterilizing the embolic device in a heat set shape of the embolic device. The embolic device is loaded into an introducer and the embolic device includes a proximal end with a suture threaded through a fenestration machined on the proximal end. The embolic device is protruded from the introducer to allow the embolic device to assume a deployed state. A physician is then able to examine the deployed shape of the embolic device. The method also includes enabling the physician to pull the suture backward to load the embolic device into the introducer prior to delivery of the embolic device.

Additional features and advantages of exemplary implementations of the disclosure will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. For better understanding, the like elements have been designated by like reference numbers throughout the various accompanying figures. At least one of which may be drawn to scale. Understanding that these drawings depict only typical embodiments of the invention and are not therefore to be considered to be limiting of its scope, the invention will be described and explained with additional specificity and detail through the use of the accompanying drawings in which:

FIGS. 3A-3E illustrate cross-sectional views of various embodiments of embolic devices with different micro-machined fenestration patterns on the tube structure of the embolic device;

DETAILED DESCRIPTION

Figure 1:
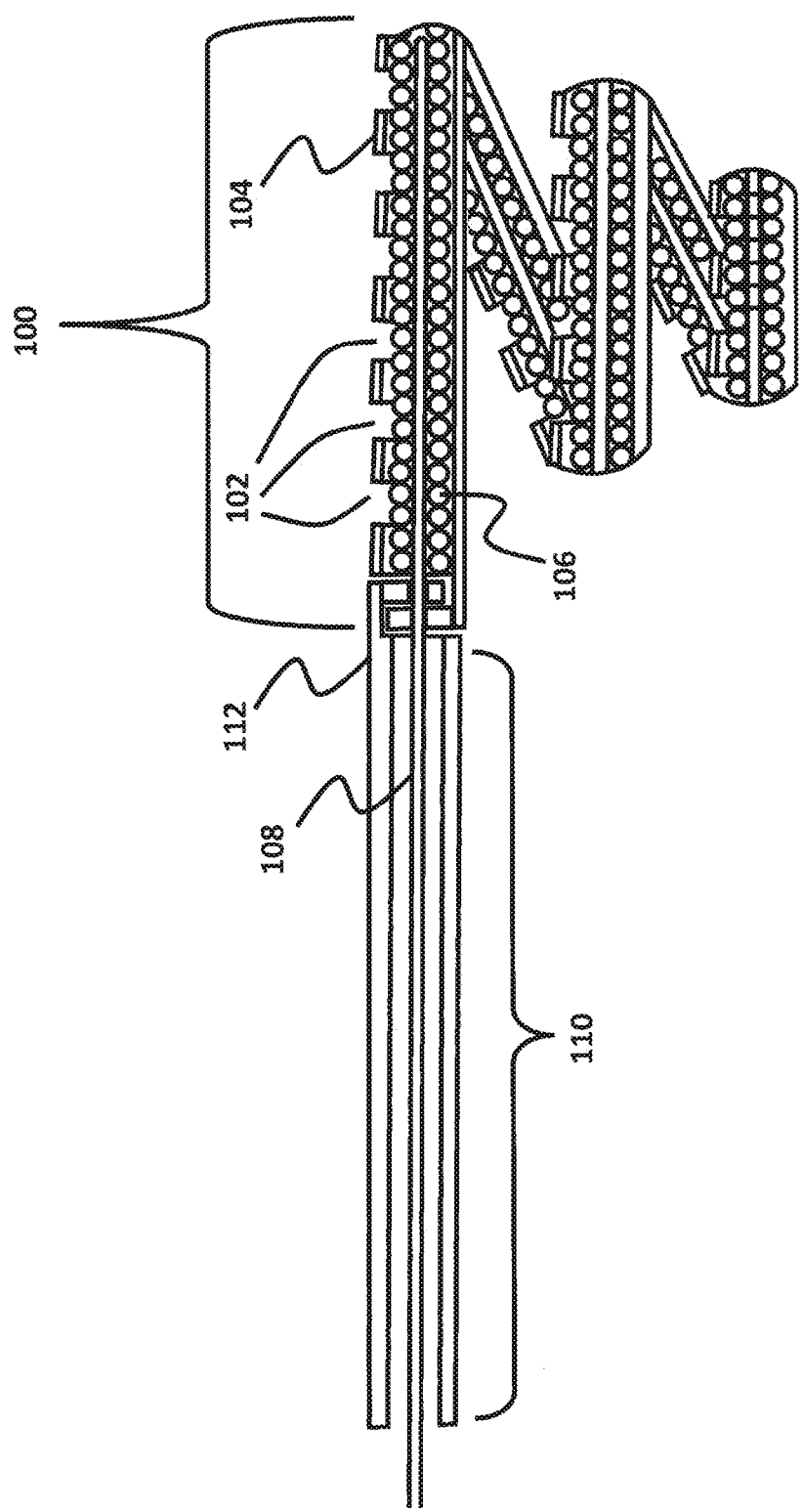
FIG. 1 illustrates a cutaway side view of a controlled delivery embolic device in accordance with an embodiment.

Embodiments may be directed to endovascular vessel occlusion by using embolic devices with improved thrombogenic materials and with long-term stability to prevent future vessel re-canalization. In embodiments described herein, micro-fabrication techniques may be used to create embolic devices by machining details into the walls of a tube structure and fitting a coil inside the tube. Embodiments of the embolic device described herein may leverage the ability to machine micro features in the tube structure, a capability that no other embolic coil has demonstrated or attempted. The micro-machining of the tube of the embolic device results in greater advantages compared to existing embolic coils by providing mechanical features, chemical features, biologic features, geometric features, material features, and pharmaceutical design options, among others. For example, micro-machining may create a flow trip (i.e. a boundary layer that changes the fluid dynamics from a laminar flow to a turbulent flow). Tripping the blood flow may create eddy currents, stagnation, or other flow dynamics that may increase the effectiveness of the embolic coils.

The micro features machined into the wall of the tube provide both flexibility as well as windows that expose the interior of the tube and the inner coil to tissue and bodily fluids. The micro-machined windows (also referred to as fenestrations) may be fixed in size, but they may change in size and shape somewhat upon flexing. The windows provide communication to the interior of the embolic device, allowing blood and other tissues access to any material or agent disposed within the embolic device. The fenestrations also provide surface space and features for tissue in-growth and fixation.

The fenestrations in the tube structure of the embolic device may result in rings (or links) formed between the fenestrations. The sizes of the fenestrations can vary in an embolic device. For instance, a first fenestration may have a first length and a first width, while a second fenestration adjacent to the first fenestration may have a second length and a second width different than the first length and the second width. In addition, a first series of adjacent fenestrations may have similar dimensions, while a second series of adjacent fenestrations may have dimensions that are different from the dimensions of the first series of adjacent fenestrations. Similarly, within a sequence of fenestrations, the dimensions of the fenestrations may alternate between two or more dimensions. The first fenestration may have a first set of dimensions, the second fenestration may have a second set of dimensions, the third fenestration may have the first set of dimensions, and the fourth fenestration may have the second set of dimensions, and so on. The fenestrations (or windows) may also be described as an angle around the circumference of the tube structure to cut (the depth of the cut), and the length of the cut. Varying the angle along the length of the fenestration may be used to create fenestrations with varying cut angles.

The tube of the embolic device may be manufactured by micro-machining slots to a specific depth in the tube structure. The depth of the micro-machined slots may be selected to allow for adequate flexibility, strength, and shape retention. Features may also be micro-machined at the proximal end and/or the distal end of the embolic device to allow for suture-loading of the embolic device into the introducer, as described further in detail below.

The embolic device may be provided in several different sizes and shapes that are heat set into specific geometries. Embolic devices may be set into a plurality of geometries that are standard for peripheral embolic devices. In addition, embodiments of the micro-machined embolic devices may also be shaped into a wider variety of geometries that optimize vessel occlusion.

An embodiment is directed to an embolic device comprised of a coil made of a first material and disposed on the inside of a tube structure made of a second material. In one embodiment, the embolic device may be comprised of a tantalum coil on the inside of a polyetheretherketone (PEEK) tube. PEEK is an organic polymer thermoplastic. Specifically, it is a semi-crystalline, high temperature thermoplastic that is ideal for use in catheters due its high modulus of elasticity resulting in torqueability and resistance to deformation. PEEK may also be combined with other types of polymers, such as polyether block amide (PEBA), carbon fibers, and glass fibers. In particular, the PEEK tube may provide a micro-machined delivery implant frame (and may be doped for improved radiopacity), while the internal coil may provide radiopacity and thrombogenicity. While embodiments described herein may reference a PEEK tube, a material other than PEEK may be used for embodiments of embolic devices without departing from the spirit of the invention. The tube may also be made out of high modulus materials, such as polymers and even polyethylene.

The coil may be a wire wound to a specific coil or spring dimension such that it fits inside the tube structure. The coil may be secured to the tube structure by encapsulating its ends into melted ends of the tube structure. Alternatively, an adhesive may be used to secure the coil to the tube structure. Methods for securing the inner coil within the tube structure of the embolic device are described in detail herein. It is also to be understood that the coil may be disposed within a tube structure made of a material other than PEEK. Similarly, a coil made of a material other than tantalum may be disposed within a PEEK tube structure, or within a tube structure made of some other material. In some embodiments, both the tube structure and the coil may be made from the same material. For example, both the tube structure and the coil may be made from PEEK.

Prior embolic coils do not employ tantalum coils because tantalum coils are not as strong as some other materials. However, in the present embolic devices, the strength of the tantalum is not a limiting factor because the tube structure helps maintain the shape of the tantalum coil. The embolic device thus provides a way of using a tantalum coil without the limitations that may be introduced by its comparatively lower overall strength.

The tube material may be doped to provide new material and/or biological properties and other features. Radiopaque dopants may be added for additional visibility. Thrombogenic materials (such as glass fibers) may be compounded to the tube structure to further increase its thrombogenicity. Biosensitive materials may also be used to enhance particular properties and create particular effects when the embolic device is deployed. For instance, materials that increase the ionic sensitivity of the PEEK tube may be used to further enhance the electropositive effects of the embolic device.

PEEK typically has a modulus of around 600 kilo-pounds per square inch (kpsi) to 800 kpsi. With the addition of glass or carbon fibers to the PEEK material, the modulus may be increased to provide new material properties, and consequently provide new embolic designs. For instance, a modulus of 1.5 Mpsi may provide for the reduction in size of some of the coil features. This may change flex, window size, shape, shape retention, etc., which would expand the design window of embolic devices.

Doping the tube material with glass fibers may result in the tube having a surface material that is more thrombogenic than the tube material alone. The micro-fabrication process for forming the fenestrations on the tube may also expose the doping material at the surface (if not already exposed). This material will contact the blood and other tissue in the body. The doping (sometimes referred to as "filling" or "loading" in the compounding and extrusion industries) of the tube with glass fibers has the benefit of increasing the modulus of the tube, while at the same time increasing the thrombogenicity of the tube. The doping of the tube material may be done using various doping and synthesis processes.

In one embodiment, the fenestrations of the tube structure may involve thermo-forming all the fenestrations at once. The process works similarly to a polymer mold, and may begin with industrial polymer pellets in place of the previously extruded stock material. Industrial polymer pellets may be poured into a mold shaped with the desired product structure including the desired resultant beam widths, the desired pattern of beams along the x-axis, and the desired lumen in the case of a catheter. The mold and the polymer pellets set in the mold may then be heated above the melting temperature of the particular polymer pellets, flowing the melted polymer into place within the product structure mold. The polymer may then be cooled, or allowed to cool, and the formed product removed. Thus, an embolic device may be formed without having to micro-machine individual fenestrations along the entire length of the tube stock material. In particular, the polymer pellets may be mixed with glass fibers, glass pellets, carbon fibers, carbon pellets, etc. to make a tube structure with infused materials.

The embolic device may be a simple, pushable, non-retrievable embolic device delivered through a catheter to a specific location. The embolic device may be loaded into the proximal or distal end of a delivery catheter, and a plunger or pusher device may be used to deliver the embolic device to the delivery site. Alternatively, the embolic device may be a controlled-delivery embolic device. The controlled-delivery embolic device includes a moveable internal shaft that provides a concentric connection between the coaxial pusher and the micro-machined embolic device. The internal shaft enables the embolic device and the coaxial pusher to move as one unit that a physician can use and control similarly to a guide wire. An embodiment of a controlled-delivery embolic device is described in reference to FIG. 1.

Embodiments of embolic devices described herein may be loaded with a plurality of fibers disposed within the inner coil. An embolic device may be loaded with glass fibers, polyester fibers (such as DACRON® fibers), and hydrophilic polymers. The use of fibers improves the thrombogenicity of the embolic device (and consequently improves clotting), by increasing the surface area that comes in contact with tissue and bodily fluids. Better filling and/or holding force may be achieved by the better interconnection provided by the fiber within the inner coil. Greater filling density may be achieved by using a swelling polymer after embolic device placement. As described further in detail below, the inner fiber may be loaded with autologous blood, with some other type of bodily fluid, or with an agent such as a fibrinogen agent, a therapeutic agent, a radiotherapy agent, a chemotherapeutic agent, etc. The fiber may also include a drug delivery coating to control the delivery rates of drugs to the treatment site.

In one embodiment, the tube is micro-cut and a flexible elastomeric material, such as PEBA, may be used as a laminate filling. Such a combination of a PEEK tube and a PEBA laminate filling may be advantageous because PEEK has a modulus (stiffness) of approximately 3700 MPa, while PEBA has a modulus of approximately 10 to approximately 500 MPa (depending on production considerations). As a result, the flexibility of the micro-cut skeleton or substructure will hardly be affected by the addition or inclusion of a much more highly flexible laminate skin or matrix.

In an embodiment, a liner or TEFLON® coated mandrel (or NITINOL® mandrel) may be inserted into the hollow central area of the tube, such that the tube and liner melt together when heat is applied to the tube. For example, PEEK has a melting point of approximately 343 degrees centigrade and PEBA has a melting point of approximately 134 to 174 degrees centigrade depending on how exactly the PEBA was produced. Therefore, a liner formed of, for example, PEBA may be inserted into either a portion of, or the entire length of the tube of, for example, PEEK, and then the combination may be heated to 175 degrees centigrade (or to the necessary temperature) to form the combined sleeve. If the PEEK sleeve has been micro-machined, then the PEBA laminate may melt into and at least partially fill the fenestrations between the rings of the sleeve, the PEEK rings and resultant beams will not melt and remain approximately unaltered. Alternatively, a tube may be pulled over the exterior of the PEEK sleeve, such that when heat is applied to the tube and sleeve, the tube and sleeve melt together forming the combined sleeve. The features of the PEEK tube may also be micro-machined after the PEEK tube has been melted with the liner or Teflon coated mandrel.

In one embodiment, the partial filling of the fenestrations of the tube may be performed as follows. When it is desirable to at least partially fill the fenestrations with PEBA (or with some other material), the PEBA may be melted with the sleeve as indicated above, but with a temporary inner coil on the inside of the tube. After the PEBA has been melted and at least partially filled the fenestrations, the temporary inner coil may be pulled out of the tube structure. Finally, the actual inner coil may be inserted into the lumen of the tube structure (previously occupied by the temporary inner coil). In particular, the at least partial filling of fenestrations improves the shape retention features of the embolic device.

The at least partially filled fenestrations may be used to increase the stiffness along portions of the sleeve and also to provide spongy pushback either while the embolic device is straightened or when the embolic device is in its deployed shape. As an example of the above described laminate layer, FIG. 3A illustrates an embolic device 300 having an elastomeric laminate layer 360 shown at least partially filling some of the fenestrations of the device 300. By selecting various modulus materials for the hybrid walls, additional flex features are possible. A tube with at least partially filled fenestrations or a tube that is closed may be used for the fixation of other agents in the embolic device, such as agents for radio therapy or chemotherapy.

FIG. 1 illustrates a cutaway view of an embodiment of an embolic device 100 with micro-machined fenestrations 102 formed along the top edge of the embolic device 100. The embolic device 100 is shown having a downward spiral shape, where the radius of the spiral decreases with the downward direction of the spiral. The embolic device 100 is includes a tube 104 made of a first material, with micro-machined fenestrations 102 formed on the tube 104. The embolic device includes an inner coil 106 made of a second material. In FIG. 1, the inner coil 106 is illustrated as being tightly wound, as evident from the cross-sectional loops being next to each other and with little space in between the loops. However, as described in further detail below, the coil pitch may be varied to create tightly wound inner coils, loosely wound inner coils, inner coils with variable pitch along the length of the embolic device, and combinations thereof.

An inner wire 108 runs along the center of the inner coil 106. The inner wire 108 helps maintain the shape of the embolic device 100 while on the shelf, while the inner coil 106 supports the memory of the tube 104. In the embodiment illustrated in FIG. 1, the inner wire 108 is also used for locking the embolic device 100 with the pusher/delivery device 110. The delivery device 110 has a distal end 112 that may interlock with the proximal end of embolic device 100. The inner wire 108 is threaded through the center of the interlocking ends of the delivery device 110 and the embolic device 100, locking these two components together and preventing the embolic device 100 from separating from the delivery device 110 during delivery.

Figure 2A:
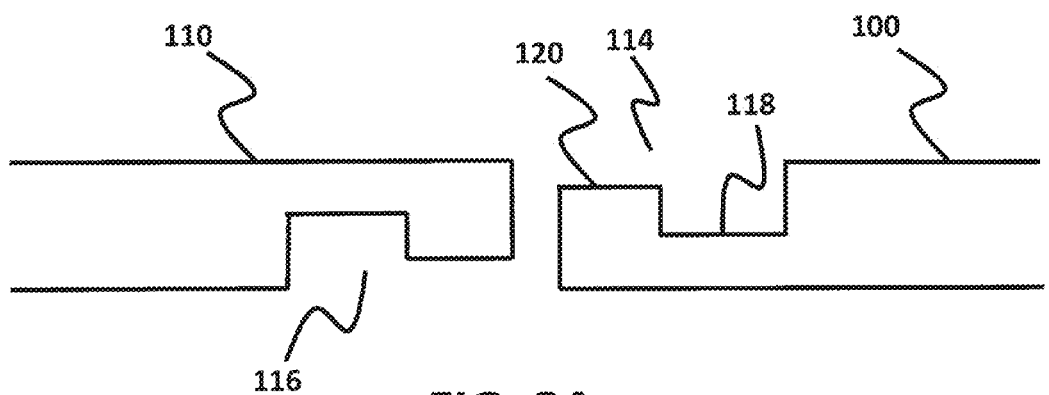
FIGS. 2A and 2B illustrate a cross-sectional view of an embodiment of a detachment mechanism that may be used for delivery of the embolic device from FIG. 1.

FIG. 2A illustrates a cross-sectional view of an embodiment of a detachment mechanism that may be used for embolic device 100. Other detachment mechanisms are also contemplated. For example, electrolytic detachment, such as a GDC coil, may be used. Furthermore, embodiments of the embolic devices used herein may be deployed without a detachment system. For instance, an embolic device may be simply pushed out of a catheter or other delivery device.

The embolic device 100 may include a substantially rectangular hook shaped end (facing up) on the proximal end 114 of the embolic device. Similarly, the delivery device 110 may include a complimentary end 116 having a substantially rectangular hook shaped end (facing down) on the distal end of the delivery device 110 that engages with the proximal end 114 of the embolic device 100. As illustrated in 2B, the hooks of the aforementioned ends 114, 116 may include an indented portion 118 and/or a raised portion 120, where the raised portion 120 of the embolic device 100 is sized and shaped to fit and engage the indented portion 118 of delivery device 110 and vice-versa.

Figure 2B:
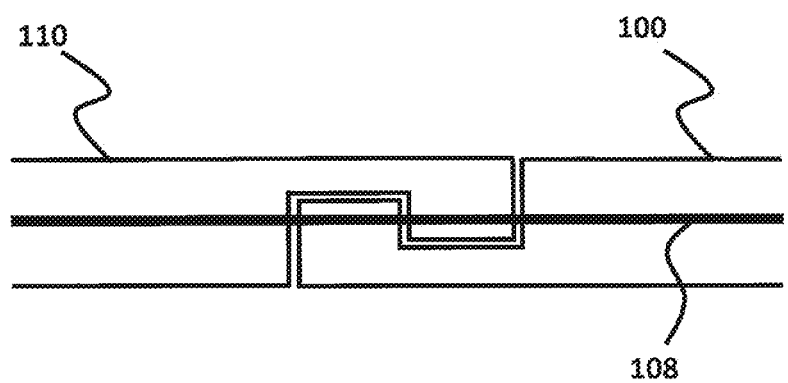

Inner wire 108 may be threaded through the interlocking ends of embolic device 100 and delivery device 110. FIGS. 2A and 2B do not show the inner coil 106, but as illustrated in FIG. 1, the inner wire 108 may threaded through the center of inner coil 106. The inner wire 108 may secure the embolic device 100 and the delivery device 110 and may prevent them from separating as the embolic device 100 is pushed through a catheter to the delivery location. Once the embolic device 100 is positioned at the delivery site, the inner wire 108 is pulled back along the length of the embolic device 100 until it reaches the interlocking ends of the embolic device 100 and the delivery device 110. When the inner wire 108 is pulled back past the interlocking ends, the embolic device 100 separates from the delivery device 110. Therefore, the inner wire 108 may be a temporary part of the embolic device 100 that aids during delivery and deployment, while helping maintain the shape of the embolic device while on the shelf.

While FIGS. 1 and 2 illustrate the use of a particular detachment system and method, embodiments of embolic device may use any alternative detachment system and method used with prior embolic coils.

In one embodiment, the tube may be micro-fabricated by performing cuts along a single side of the tube, as opposed to making simultaneous cuts on opposite sides of the tube. Forming cuts along a single side of the tube may result in a continuous, uncut spine formed opposite the micro-machined fenestrations. For example, FIG. 1 illustrates embolic device 100 having a tube 104 with micro-machined fenestrations 102 formed along the top of the tube 104, leaving a continuous, uncut spine (without fenestrations) along the bottom of the tube 104. Cutting the embolic coil 100 along the top portion of the tube 104 may result in the embolic device 100 having a preferred orientation for bending. Thus, altering the cutting pattern of the embolic device may be used to control and alter the preferred orientation of bending of the embolic device and/or of the deployed state of the embolic device. The micro-fabrication of the embolic device also enables the embolic device to fold on itself, which in prior embolic coils was an undesirable feature. Folding on itself may be advantageous in facilitating occlusion.

Embodiments of the micro-fabricated embolic devices may leverage the folding of the embolic device to provide structures that were not possible with prior embolic coils. The structure and properties of embodiments of embolic devices described herein result in rapid embolic occlusions due to increased thrombogenicity and increased density. At least one embodiment of the embolic devices described herein also require the use of fewer embolic devices to occlude an area. In contrast, prior embolic coils required more embolic coils to occlude an area, resulting in a more costly solution, in addition to also increasing the risks of the aneurysm rupturing, recurrence of the aneurysm, or another aneurysm forming near the occluded aneurysm.

FIG. 3A illustrates a side view of the micro-fabricated tube of an embolic device 300 in accordance with an embodiment. Embolic device 300 is shown with a sequence of four uniform micro-machined fenestrations 302, resulting in five rings 304, followed by a large spacing window 306, which is followed by the same pattern of four uniform fenestrations forming five rings, and so on. The large spacing windows may be used to make folding spots on the embolic device, allowing the embolic device to fold onto itself. The fenestrations 302 all made along a single side of the embolic device 300 may result in a continuous, uncut spine 308 formed opposite the fenestrations 302. The micro-fabricated pattern illustrated in FIG. 3A may be repeated along the length of the embolic device 300. Alternatively, the pattern illustrated may be repeated along a portion of the embolic device, while using a different pattern along a different portion of the embolic device.

FIG. 3B illustrates an embolic device 310 with a different micro-fabricated pattern of fenestrations. The micro-fabricated pattern of FIG. 3B consists of a set of two uniform micro-machined fenestrations 312, resulting in three rings 314, followed by a larger spacing window 316, and followed by the same pattern of two uniform fenestrations forming three rings. Similar to embolic device 300, cutting the embolic coil 310 along a single side results in a continuous, uncut spine 318 formed opposite of the fenestrations 312. The resulting shape of embolic devices can thus be controlled by varying one or more of the following: the number of micro-machined fenestrations, the spacing between micro-machined fenestrations, the depth of the micro-machined fenestrations, the cutting angle of the blade forming the micro-machined fenestrations, the uniformity or randomness of the micro-machined fenestrations, the number of spacing windows, the length and depth of the spacing windows, etc. Thus, the present disclosure contemplates embolic devices with any combination of the following. For example, an embolic device with varied number of micro-machined fenestrations, varied cutting angle of the blade forming the micro-machined fenestrations, varied uniformity or randomness of the micro-machined fenestrations, varied number of spacing windows, varied length and depth of the spacing windows, other features, and combinations thereof.

Other methods for controlling the shape of an embolic device include using the same cutting pattern throughout the entire length of the embolic device and varying the cutting pattern along the length of the embolic device. For example, FIG. 1 illustrates embolic device 100 having a set of uniform micro-machined fenestrations 102 along the length of the embolic device 100, where larger spacing windows are used to create folding points that give the embolic device 100 its downward spiral shape.

Embodiments described herein thus enable the micro-machined cutting pattern of an embolic device to form particular shapes by allowing the embolic coil to bend in one or more particular directions along one or more sections of the embolic coil. The cutting pattern may be used to create embolic coils that form a particular shape. In addition, an embolic device may be micro-cut to optimize the strength of the entire device, the strength of particular sections of the embolic device, the flexibility of the entire embolic device, the flexibility of particular sections of the embolic device, the stiffness of the entire embolic device, the stiffness of particular sections of the embolic device, or other physical characteristics of the embolic device.

For example, the micro-fabrication of fenestrations on the embolic device allows for the selection of flexibility based on the needed coil design. Softer or firmer coils may be produced from the same base material, without a new coil wire or wire size, simply by machining different features in the tube structure. On the other hand, prior embolic coils required the use of different coil wires and different wire sizes to create embolic coils with different flexibility properties. Additionally, larger tubes typically have less flexibility than smaller tubes. However, the micro-fabrication process allows for the flexibility of larger tubes to be increased without changing the tube diameter. The stiffness of the entire embolic device or of portions of the embolic device may also be designed by varying the spacing between fenestrations and the depth of each fenestration, as well as by varying the durometer of the elastomeric material used in the lamination.

The micro-fabrication process also allows the flexibility along the length of a coil to be varied in arbitrary lengths and in any order. For example, an embolic coil may be micro-fabricated to have discontinuous flexibility, or to have flexibility that varies from soft to firm along the length of the embolic coil, or that varies from firm to soft along the length of the embolic coil. This capability may allow for contouring flexibility along a coil shape in order to conform the embolic coil to anatomical features. For instance, a firmer embolic coil may be used for fistula or an artery ostium, while a softer embolic coil may be used for the dome area of an aneurysm. Having variable flexibility along a length of the coil, with the ability to vary the flexibility in arbitrary lengths and in any order may enhance shape assumption and shape recovery upon delivery. For instance, increasing the flexibility at various points of the embolic device may be used to allow for folding at particular points of the embolic device. As noted above, providing an embolic device that folds into itself may allow the embolic device to assume a shape that provides denser occlusion in a vessel compared with prior and traditional embolic coils.

The exterior of the inner coil may be continuous, and therefore keeping the inner coil from stretching like standard coils. For example, the coil can be stretched, such that gaps form between adjacent coil wires, rather than stacked, such that the adjacent coil wires abut. This ability to stretch rather than stack allows the coils to be pushed. Typical coils that include gaps generally stack and do not deploy very well as they typically do not hold their shape, thereby reducing their pushability.

Figure 3C:
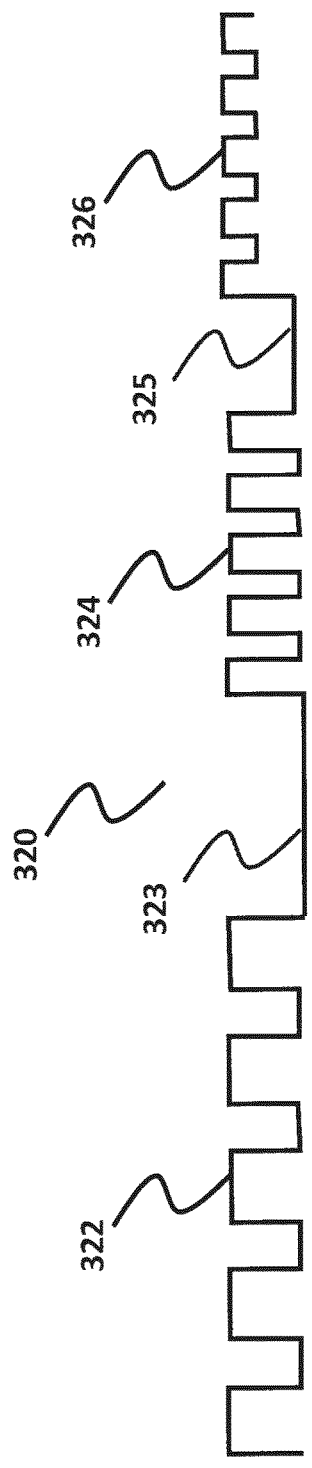
Figure 3D:
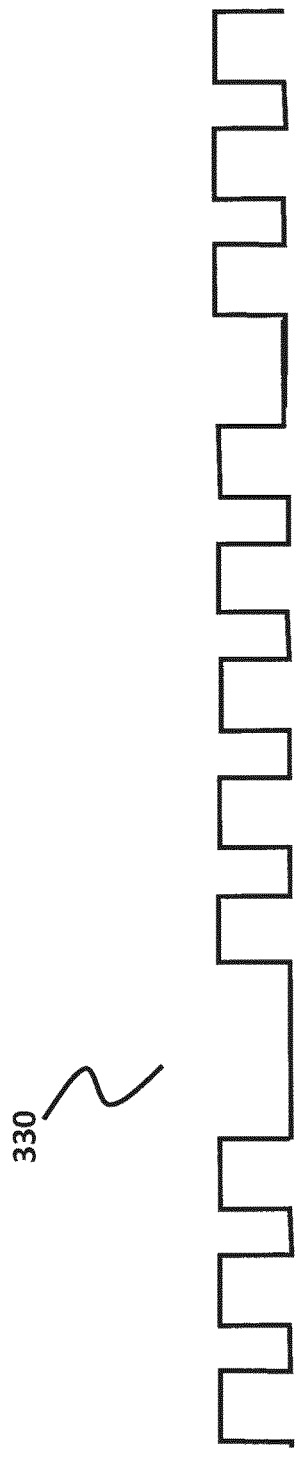

FIGS. 3C and 3D illustrate embolic devices with varying cutting patterns. For example, a first cutting pattern may be repeated along some sections of the embolic device, while a different cutting pattern may be repeated along other sections of the embolic device. FIG. 3C illustrates an embolic coil 320 with a first cutting pattern 322 consisting of four fenestrations, resulting in five rings. A spacing window 323 separates the first cutting pattern 322 from the second cutting pattern 324, with the second cutting pattern consisting of four narrower fenestrations. Finally, yet another spacing window 325 separates the second cutting pattern 324 from the third cutting pattern 326. The third cutting pattern 326 consists of four fenestrations that are the same width as the fenestrations of the second cutting pattern 324, but differ in depth.

It is to be further understood that a cutting pattern need not consist of identical micro-machined fenestrations. For instance, a first cutting pattern may consist of fenestrations where each fenestration is different in shape and size than any other fenestration in the pattern. The fenestrations may increase in size along the length of the embolic device, may decrease in size along the length of the embolic device, may vary randomly along the length of the embolic device, may vary on the basis of a function, or may vary on the basis of a probability distribution. FIG. 3D illustrates yet another example of a cutting pattern of an embolic device 330 where the cutting pattern alternates from two micro-machined fenestrations to four micro-machined fenestrations, and where the spacing windows also vary in size.

As noted above, FIGS. 3A-3D illustrate examples of embolic devices that are micro-machined to have fenestrations along one side of the embolic device, forming a single continuous, uncut spine opposite the fenestrations. FIG. 3E illustrates a side view of the tube of an embolic coil, where the fenestrations rotate about the circumference of the embolic device, resulting in the uncut spine also rotating around the circumference of the embolic device. Thus, the fenestrations rotate along the length of the tube, with an offset from fenestration to fenestration dictated by an offset angle that may be constant, may change along one or more portions of the embolic device, may be random, or may be a constant plus a small randomized factor. The rotation of the fenestrations thus results in the fenestrations moving along the circumference of the embolic device. The fenestrations may also rotate in sets. For instance, five window fenestrations may be made along the top side of the sleeve, with the next five fenestrations made at an offset angle, and so on.

In embodiments of the embolic device with a continuous, uncut spine formed "opposite" of the fenestrations, it is to be understood that the uncut spine need not be opposite the fenestrations. That is, a fenestration may also be defined as an angle around the circumference of the tube and a length. For instance, a 350 degree fenestration would consist of a window that spans over 95% of the circumference of the tube, leaving about 10 degrees of the tube circumference as a spine. The spine is thus the circumference of the tube that is left uncut. For instance, a 10% fenestration cut would leave a 90% spine.

FIG. 3E illustrates a side view of embolic device 340 with the fenestrations rotating along the circumference of the embolic device 340. For illustration purposes, it is assumed that embolic device 340 was micro-machined with uniform fenestrations. In FIG. 3E, the top side 342 is to be assumed 0 degrees around the circumference of the tube of the embolic device, while bottom side 344 is assumed to be 180 degrees around the circumference of the tube of the embolic device. The top side 342 of the embolic device includes fenestrations 346, forming rings 348, which slowly rotate around the embolic device, eventually resulting in fenestrations 350 (forming rings 352) on the bottom side 344 of the embolic device. For example, a first fenestration may be made at 0 degrees along the circumference of the embolic device, the next fenestration may be a distance apart from the first fenestration, but offset by five degrees (or offset by any some other degree). The next fenestration may also be offset by some degrees, and so on. This would result in the fenestrations rotating around the circumference of the embolic coil, along the length of the embolic device. It is noted that the size of the fenestrations, and the offset angle from fenestration to fenestration, may vary to create an embolic device with a desired shape and with desired properties. For example, the pattern of fenestrations depicted in FIG. 3E may result in a preferred orientation to the flexibility of the embolic device and partially create a deployed state having a continuous bend such as a spiral or a circular structure.

When machining embolic coils having only a single cut per side of the embolic coil, a machine as described in commonly assigned U.S. patent application Ser. No. 12/633,727, which is incorporated herein by reference, may be used, using only one blade to perform the cuts, rather than using two blades making cuts opposite each other.

As an embolic device is deployed, it folds into a particular shape. The manner in which the embolic device folds is determined by the tube material, the inner coil material and shape, the cutting pattern of the tube, the size and shape of the fenestrations of the tube, the size and shape of the spacing windows, the arrangement of the spacing windows, etc. Specifically the spacing windows make folding, or hinging, spots that make the embolic device fold about that point. Typically, embolic coils are deployed having a helical shape, and any kinking or folding as described above is undesirable. However, embodiments described herein enable embolic devices to assume non-helical shapes by the fabrication of the folding points.

Embolic devices with non-helical shapes are desirable to create embolic devices that efficiently occlude the diameter of a vessel by making the embolic device fold and fill the center of the vessel. Hence, rather than deploying an embolic coil that is helical and that is substantially long and with an empty center, embodiments described herein may comprise of embolic devices consisting of a few loops forming an anchor against the vessel wall, and a high volume of the embolic coil folding into the center of the outer loops. The size of the spacing windows in the cutting pattern of the embolic device may be fabricated based on the diameter of the area to be occluded.

The use of the spacing windows to form folding points also results in embolic coils that can effectively occlude an area while occupying less volume. For instance, rather than occluding an artery by using a helical coil that is 2 cm long, embodiments of embolic devices as described herein result in smaller, but dense shapes that improve clotting.

Figure 4A:
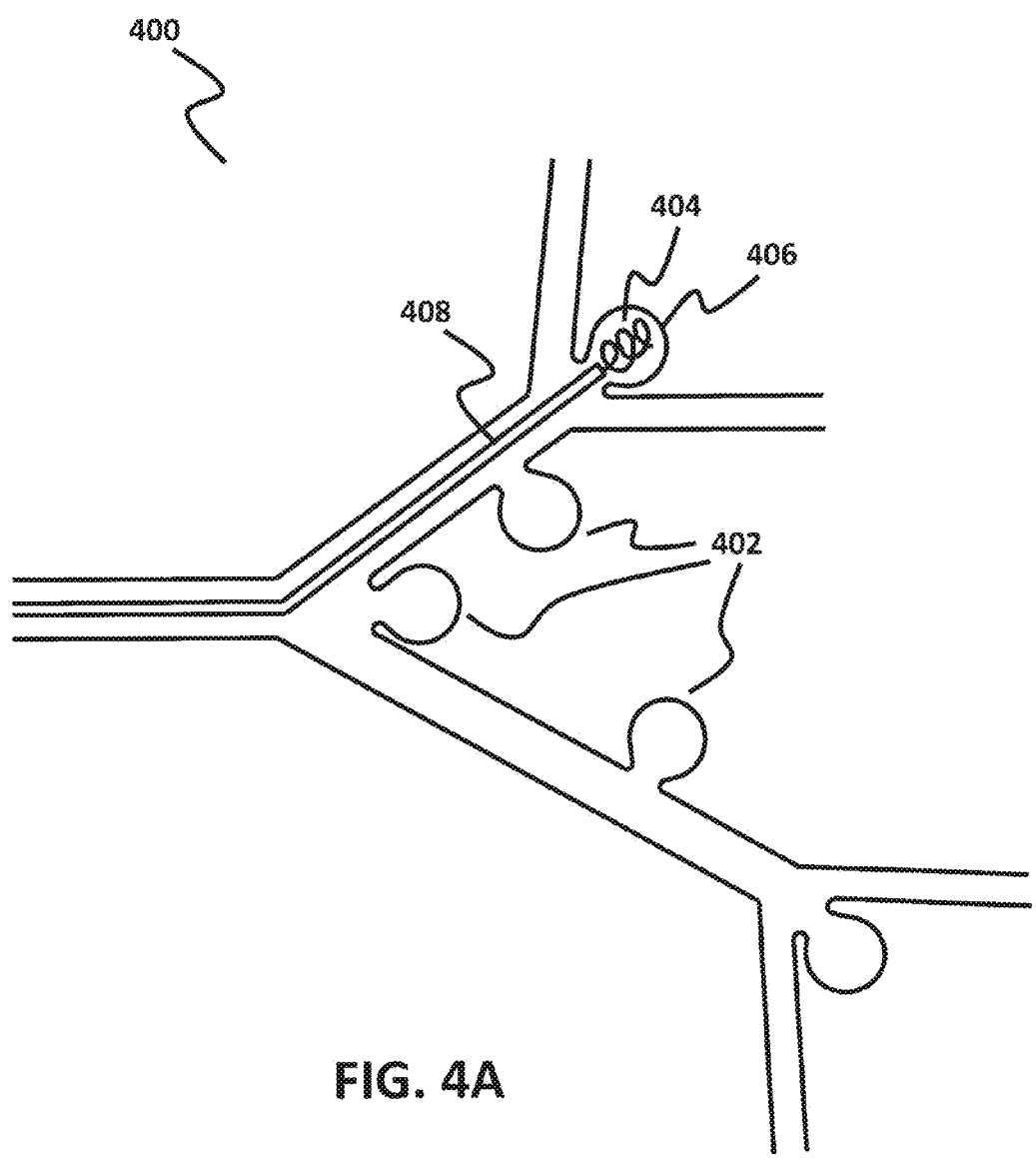
FIG. 4A illustrates an artery model with a number of aneurysms.

FIG. 4A illustrates an artery model 400 including a number of balloon-like aneurysms 402. An aneurysm is a localized, blood-filled balloon-like bulge in the wall of a blood vessel (artery, capillary, or vein). It is a permanent and abnormal widening, or ballooning, of a portion of a blood vessel due to weakness in the wall of the blood vessel. Model 400 illustrates aneurysm 402 formed on the sidewalls of blood vessels and at the junction where blood vessels split into branches. Model 400 further illustrates an embodiment of an embolic device 404 being delivered to fill aneurysm 406 using catheter 408. It is to be understood that embolic devices may be delivered using a plurality of intravascular devices. In one embodiment, the delivery device may be a macro-catheter, such as the SOCRATES™ macro-catheter, a micro-catheter, such as the PLATO MICROCATH®, or a combination of a macro-catheter and a micro-catheter. SOCRATES is a trademark and PLATO and PLATO MICROCATH are registered trademarks of Scientia Vascular, LLC.

Figure 4B:
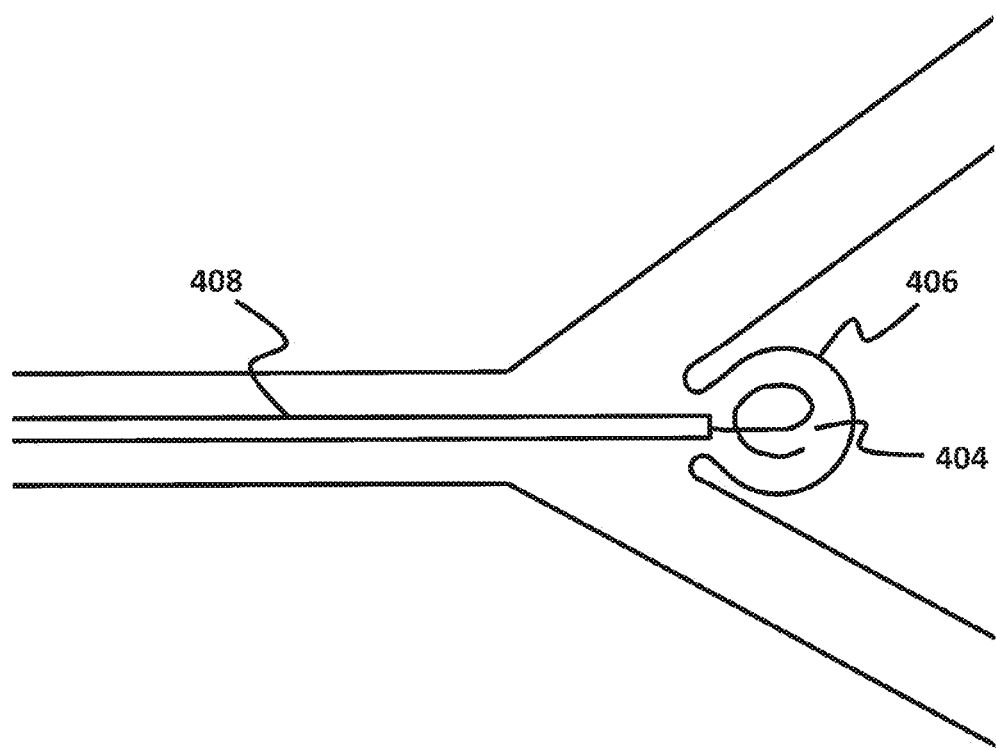
FIG. 4B illustrates a zoomed in view of an embodiment of an embolic device being delivered to an aneurysm via a catheter.

FIG. 4B illustrates in detail embolic device 404 being delivered to aneurysm 406. The catheter 408 is guided through the patient's vasculature to the area to be occluded. Depending on the delivery device, the delivery mechanism, the type of embolic coil used, or other related factors, the catheter may be moved to the mouth of the aneurysm 406 (as illustrated in FIG. 4B) or further into the aneurysm. With the catheter 406 in place, the embolic device 404 can slowly be pushed out of the catheter 408. When the entire embolic device 404 has been pushed out of the catheter, the catheter may be retrieved, or an additional embolic device may be deployed as necessary.

In embodiments of the controlled-delivery version of the embolic device, the concentric connection between the coaxial shaft and the micro-machined embolic device enables the embolic device to be navigated in and out of the catheter and into the vessel until the desired position and vessel occlusion is accomplished. Finally, controlled detachment is achieved by pulling the inner wire, which separates the embolic device from the pusher. For instance, if embolic device 404 is a controlled-delivery device, then delivery of the embolic device 404 may be monitored in case the embolic device 404 does not deployed as desired. With the concentric shaft connecting the embolic device 404 to the pusher device (not shown), the embolic device may be pulled back into the catheter 408 in order to reorient the embolic device, or to restart the delivery of the embolic device. For instance, the embolic device 404 may begin to settle in an undesired location, such as being too close to the wall of the aneurysm 406 or not deep enough in the aneurysm 406. In such a case, the embolic device 404 may be partly or entirely pulled back into the catheter 408. The delivery can then be resumed or restarted to ensure the embolic device 404 is deployed and positioned appropriately. If the embolic device 404 is a non-retrievable, pushable device, then the embolic device 404 is simply pushed out of the catheter 408, with the embolic device assuming its heat set shape as it deploys.

Figure 5A:
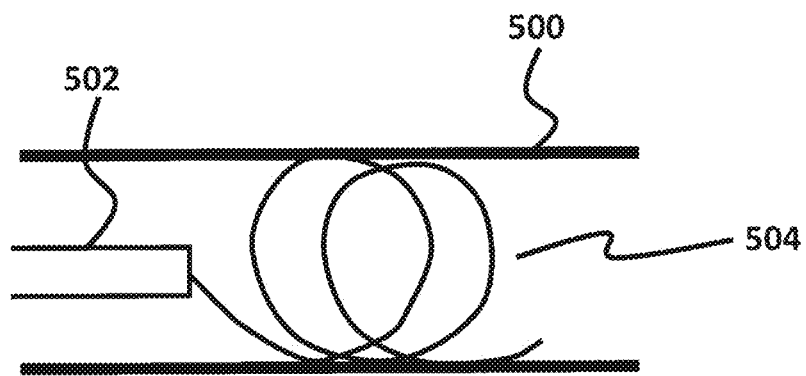
FIGS. 5A and 5B illustrate a cross-sectional view of a blood vessel being occluded with an embolic device in accordance with an embodiment, the embolic device forming a dense folding pattern that fills the center of the vessel.
Figure 5B:
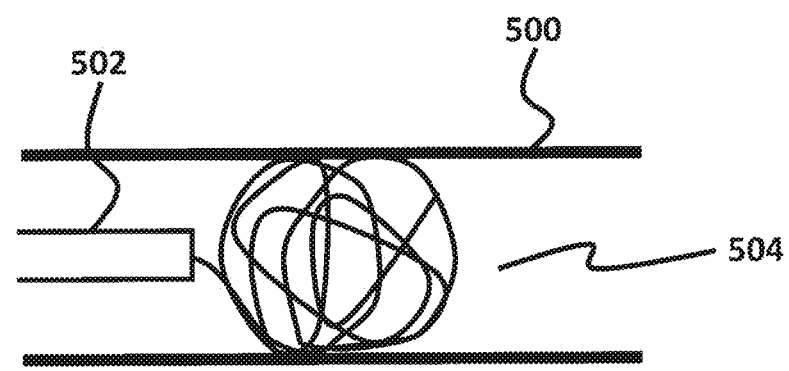

FIG. 5A illustrates a cross-sectional view of blood vessel 500. A catheter 502 is used to deliver embolic device 504 in order to block the blood vessel 500. FIG. 5A illustrates the embolic coil device deploying initially by forming two large loops having a diameter substantially equivalent to the diameter of the blood vessel 500. The purpose of these large loops is to anchor the embolic device 504 against the blood vessel wall. As the embolic device 504 is pushed out of catheter 502, the embolic device 504 begins to fold onto itself, such as by folding into the center of the two large loops, forming a kinking pattern that fills the center of the blood vessel 500 as illustrated in FIG. 5B. Thus, the initial large loops of the shape assumed by the embolic device form an outer frame that subsequently supports the folding pattern of the rest of the embolic device 504.

Embodiments thus enable embolic devices to initially deploy by forming one or more large loops that anchor against the blood vessel wall (or that anchor against one or more sections of the area to be occluded), with the rest of the embolic device forming a folding/crossing pattern extending from the edges of the loops through the center of the loops. The loops thus create an outer boundary, and the folding pattern formed by the rest of the embolic device fills the center of the loops, providing structural support for the outer loops of the embolic device shape. The forming of the initial large loops, and the subsequent folding pattern, may be controlled by using large spacing windows between the micro-machined fenestrations, as illustrated and discussed in reference to FIG. 3. The size of the spacing windows may thus be dependent on the diameter of the blood vessel or area being occluded. As has been discussed herein, embolic coils may be micro-machined as necessary to yield various lengths, shapes, sizes, diameters, and geometries.

Embolic devices described herein may be deployed as is known in the art. For instance, one embolic device may be used to block the neck of the aneurysm, while a second embolic device may be used to form a clot on the inside of the aneurysm, forming a supporting structure behind the first embolic device. If an aneurysm is large, then multiple embolic devices may be used to fill the inside of the aneurysm. Differently shaped embolic coils may also be used depending on how clotting progresses. For instance, if a first embolic device was not enough to form a clot, then a differently shaped embolic device may be used to support the second embolic device.

In embodiments disclosed herein, the embolic device is straightened as it enters the catheter and it remains straightened as it is pushed through the catheter to the delivery site. What is desirable is for the embolic device, and specifically the material used for the inner coil and the tube, to hold its shape even after being straightened while the device is within a catheter or introducer. Therefore, it is desirable for the rings/links between the fenestrations to be strong enough to hold the shape of the embolic device, but not strong enough that it results in significant plastic deformation when the embolic device is straightened. Regardless of the material used for the inner coil and tube, the embolic device is bent in the elastic range and stress relieved so that the embolic device stays in the elastic range. The embolic device may be processed such that it is elastically biased toward its deployed state. For example, the embolic device may be biased to return to a coiled shape.

In some embodiments, the outer material is cut from straight tube. The inner coil is inserted into the cut tube. The inner coil may be connected to the cut tube using adhesives, heat, or other connecting methods. Once the inner coil is inserted into the cut tube, the device may be formed into its deployed state. For example, an embolic coil may take a simple helix or a tapered coil as its deployed state. Forming the device into its deployed state may induce some plastic deformation into the device. In some embodiments, the device may be stress relieved such that the deployed state becomes the state that is "remembered." Stress relieving may be achieved by annealing the device under heat or other methods.

Thus, once the embolic filter is stress relieved, such that the deployed state becomes its "remembered" or natural, unbiased state, when it is deformed into a straight, pre-deployed state within a catheter or other device the embolic filter is biased toward the deployed state. In addition, the fenestrations may be aligned to reduce resistance when the embolic device is deployed. For example, the micro-fabricated fenestrations may rotationally align such that the tube structure creates less resistance to the embolic device attaining its deployed state when deployed. The preferred flex direction of the tube structure thereby biases the device to return to its deployed state and at least partially determines the deployed state. Plastic deformation may be minimized by packaging the coil outside of the introducer such that is sterilized and stored in its final configuration, which minimizes relaxation of the material.

Figure 6A:
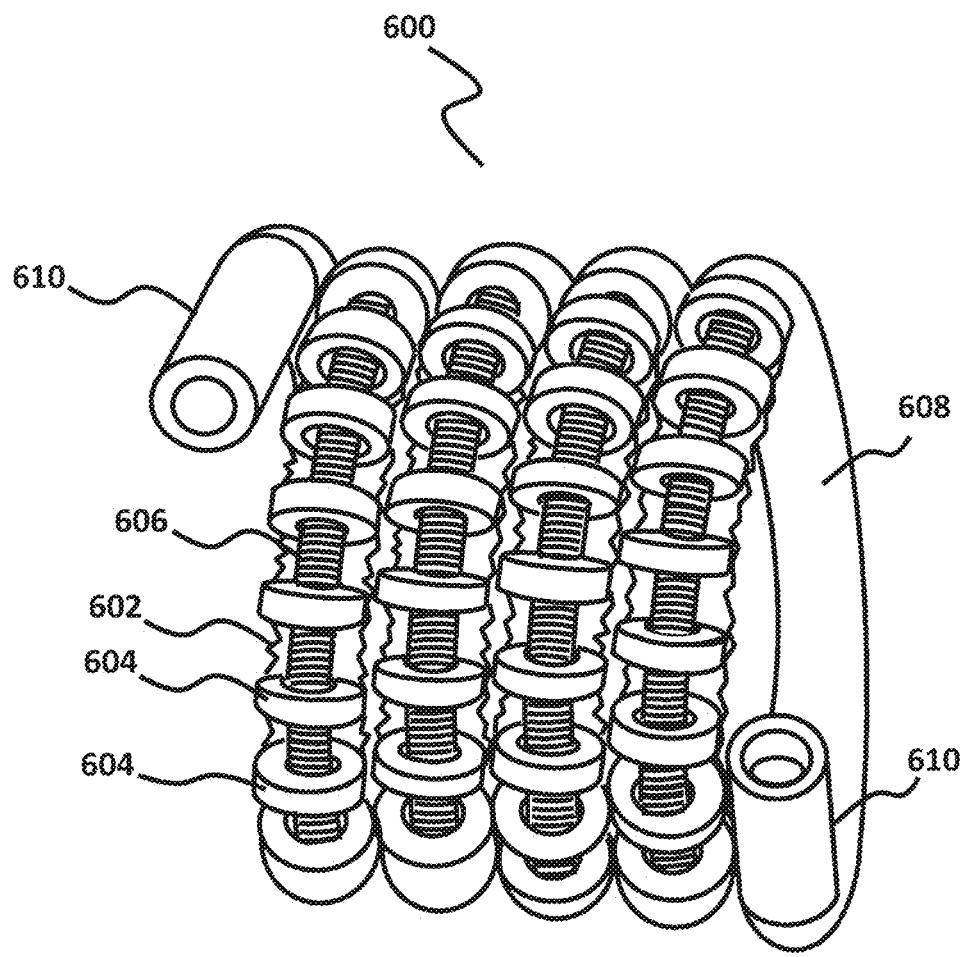
FIG. 6A illustrates a top view of an embolic device in accordance with an embodiment.

FIG. 6A illustrates a top view of yet another example of an embolic device in accordance with an embodiment. Embolic device 600 includes micro-machined fenestrations in the tube structure 602 forming resulting rings/links 604 between the fenestrations. The inner coil 606 is illustrated as being tightly wound, but in alternative embodiments the inner coil may be stretched. Alternatively, the pitch coil of the inner coil may vary along the length of the embolic coil 600. Embolic device 600 has the micro-machined fenestrations formed along one side of embolic device 600, resulting in a continuous, uncut spine 608 (the strip of tube material that is left after the fenestration has been cut). In particular, the fenestrations (formed by micro-machined cuts or by some other micro-fabrication method) enable bodily fluids and tissue to come in contact with inner coil 606 and the lumen of inner coil 606. Thus, the micro-machined fenestrations increase the surface area that comes in contact with bodily fluids and tissue, increasing the effectiveness of occluding a particular volume.

The endpoints 610 of embolic device 600 may or may not be micro-machined. In FIG. 6, the endpoints 610 are not micro-machined, resulting in the embolic device having sturdy endpoints that facilitate the pushing of the embolic device along a delivery catheter. The sturdy endpoints also enable the inner coil to be secured within the tube structure of the embolic device, as described in further detail below.

In an embolic device, the proximal and/or the distal end may be micro-machined. For example, the fenestrations can continue along the length of the endpoints of the embolic device. If the endpoint of an embolic device is to be left without fenestrations, the length of the endpoint may be set as needed. For instance, for a particular application it may be determined that the proximal endpoint is to be left without fenestrations, and that fenestrations are to begin at least 1 mm from the proximal end of the embolic device.

Figure 6B:
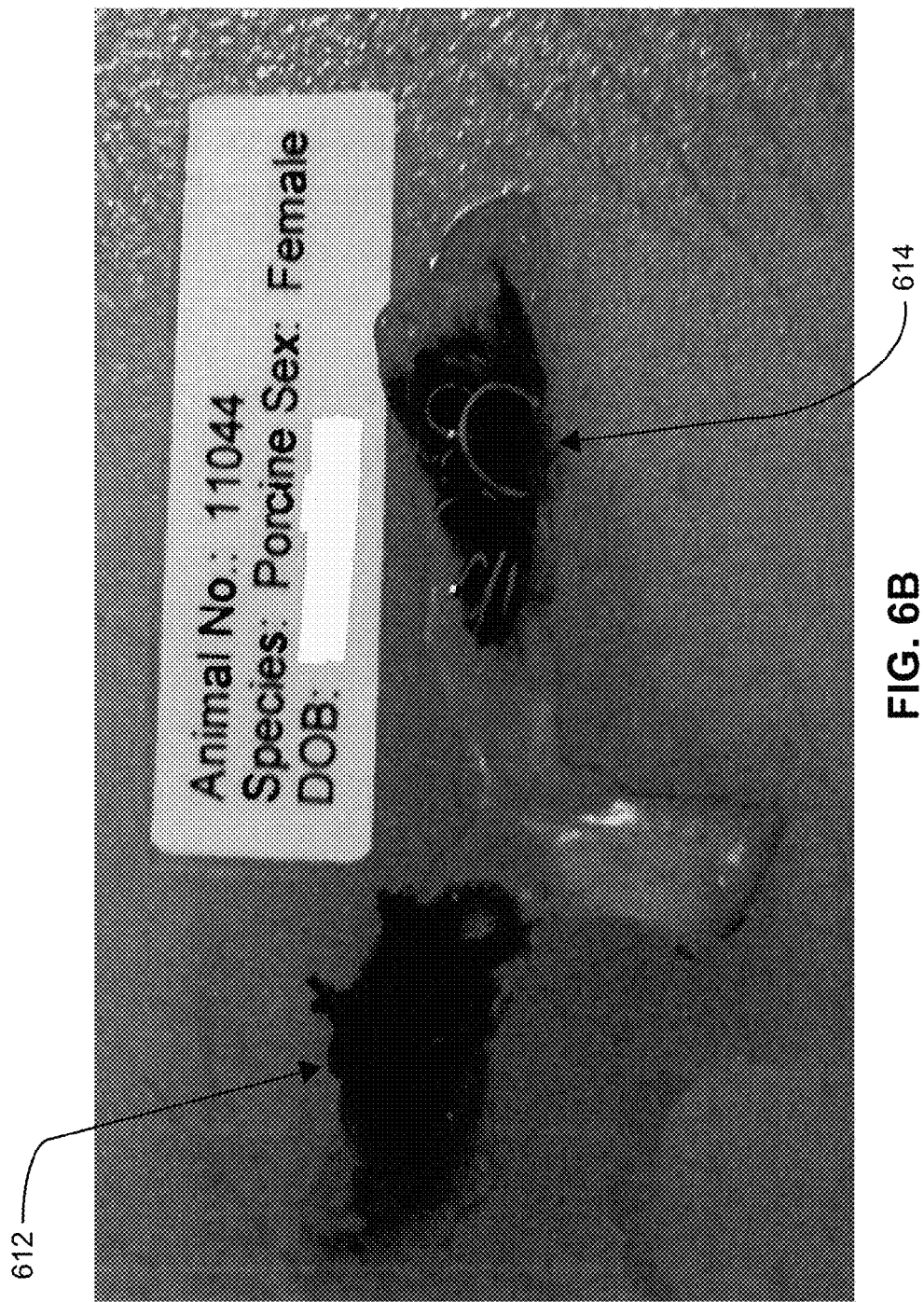
FIG. 6B illustrates a comparison the embodiment depicted in FIG. 6A and a prior art device

As mentioned earlier, the inner coil 606 may comprise a first material and disposed on the inside of a tube structure made of a second material. In one embodiment, the embolic device may be comprised of a tantalum coil on the inside of a polyetheretherketone (PEEK) tube. In particular, the PEEK tube may provide a micro-machined delivery implant frame (and may be doped for improved radiopacity), while the internal tantalum coil may provide radiopacity and thrombogenicity. FIG. 6B shows a comparison of an embodiment of an embolic device 612 in accordance with the present disclosure in a porcine blood vessel and a prior art device 614 in a porcine blood vessel. As seen, the prior art device 614 is still reflective and appears largely ineffective, while the embodiment of an embolic device 612 in accordance with the present disclosure shown on the left has created a thrombus.

Figure 7A:
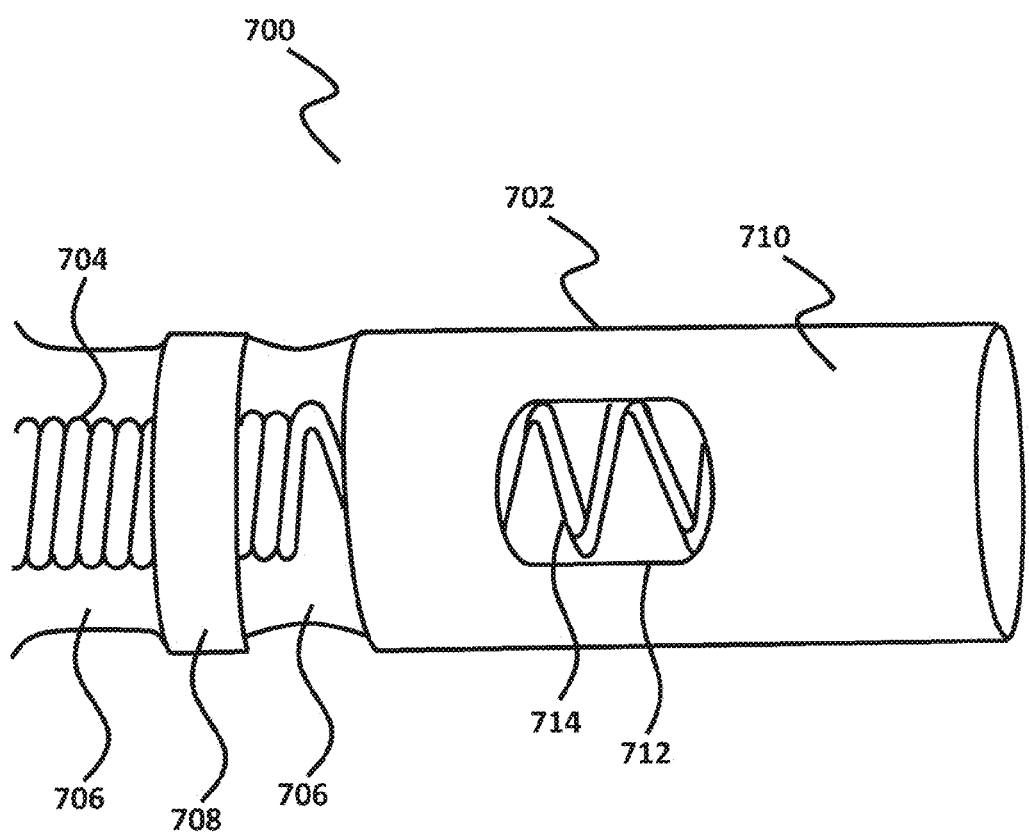
FIGS. 7A and 7B illustrate a top-down view and a bottom-up view of a distal end of the embolic device in accordance with an embodiment.

FIG. 7A illustrates a partial, top-down view of the end of embolic device 700 including tube 702 and inner coil 704. The embolic device 700 shows two micro-machined fenestrations 706, resulting in ring 708, made prior to the endpoint 710 of embolic device 700. The endpoint 710 may be the proximal end or the distal end of the embolic device. In particular, the endpoint 710 includes a top fenestration 712 formed by cutting along the lateral axis of the tube 702. Specifically, a top fenestration 712 and a bottom fenestration 718 are formed on opposite sides of the tube 702, forming a tunnel through which a suture may be threaded (with a thread, wire, or some other material) and enabling the embolic device 700 to be loaded into an introducer. The inner coil 704 is illustrated as having a variable coil pitch, with the portion of the inner coil 704 near the fenestrations 706 being tightly wound, and the portion 714 of the inner coil in the endpoint 710 being loosely wound.

Figure 7B:
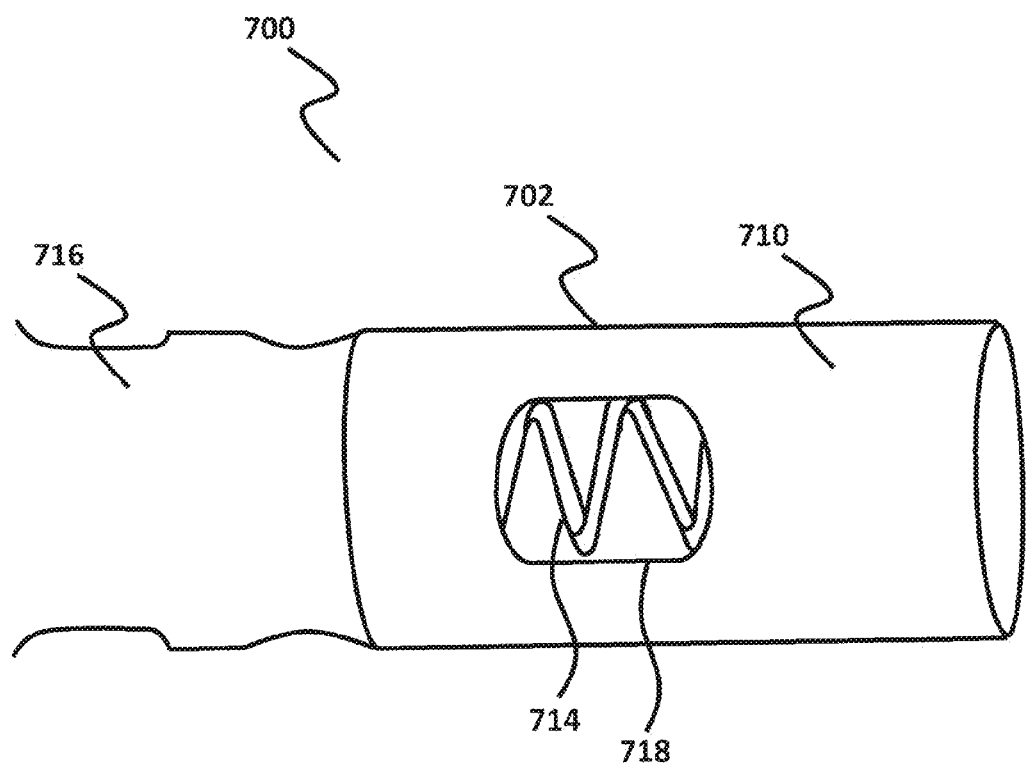

FIG. 7B illustrates a partial, bottom view of the end of embolic device 700. The bottom view illustrates the bottom fenestration 718 which in combination with top window 712 (not visible in FIG. 7B) forms a tunnel along a latitudinal axis of embolic device 700. Finally, the bottom view clearly illustrates the continuous, uncut spine 716 formed by the portion of the tube structure 702 which is left uncut.

In embodiments where it is desirable to secure the inner coil within the tube of the embolic device without an adhesive, the uncut endpoint 710 provides enough surface area to enable the ends of the embolic device to be tapered. If the end of the embolic device includes fenestrations and resulting rings, then attempts at tapering the end of the embolic device would be difficult since the narrow surface area of the ring would make the ring collapse rather than taper. Methods for securing the inner coil within the sleeve of the embolic coil will be described below.

Properties of the inner coil which may be varied include the coil pitch, the coil angle, the coil diameter, and the coil length. For instance, the inner coil need not be the same length as the tube structure. For instance, an embolic device can consist of a tube structure and an inner coil that spans only a portion of the tube structure (the length of the inner coil being less than the length of the tube structure). In embodiments where the tube structure has at least partially filled fenestrations, it may be beneficial to have an inner coil only in those portions of the tube structure with open fenestrations. The inner coil may also change in diameter along the length of the embolic device, such that the inner coil has a large diameter near the ends of the embolic device (as a method to secure the inner coil within the tube structure without the use of an adhesive), with the inner coil having a smaller diameter within some other portion of the embolic device.

In particular, the pitch of the inner coil provides an opportunity for additional product features. The coil pitch provides a secondary lumen which may be loaded and which promotes tissue in-growth. The coil pitch also provides an increased surface area, as a loose coil would expose the inside of the inner coil, while a tight coil would only expose the outside of the inner coil. Furthermore, in standard embolic coils, the coil pitch cannot be arbitrarily set because stretching, compression, and instability are highly likely and result in deformation of the embolic coil. In contrast, the inner coil of the embolic devices does not stretch and the coil pitch is maintained because the inner coil is constrained within the micro-fabricated tube structure.

Prior embolic coils are preloaded inside introducers, having written size and/or a sketch of the embolic coil on the packaging label, and with the embolic coil already loaded within the introducer. This type of packaging does not enable a physician to truly appreciate the shape that an embolic coil will assume when deployed. In addition, because the embolic coil is loaded in the introducer, the coil remains straightened while on the shelf, which can result in deformation of the coil.

An embodiment is comprised of a packaging method and/or kit allowing for the embolic device to be packaged, sterilized, and stored in its heat set shape, thereby allowing the user to inspect the embolic device shape prior to catheter introduction. For instance, a suture may be threaded through the proximal end of the device, allowing the user to simply pull the suture backward to load the device in the introducer. The suture may be removed and the device may be loaded into the proximal end of a delivery catheter with a supplied plunger device. This method has the advantage of allowing a physician to select an appropriate embolic device by examining the deployed shape of the embolic device (as opposed to examining a sketch). After a selection is made, the embolic device can pulled back into the introducer. Therefore, there is no significant potential plastic deformation of the embolic device because the embolic device is not stored in its straightened shape. The embolic device is only straightened when the device is pulled into the introducer for delivery.

Figure 8:
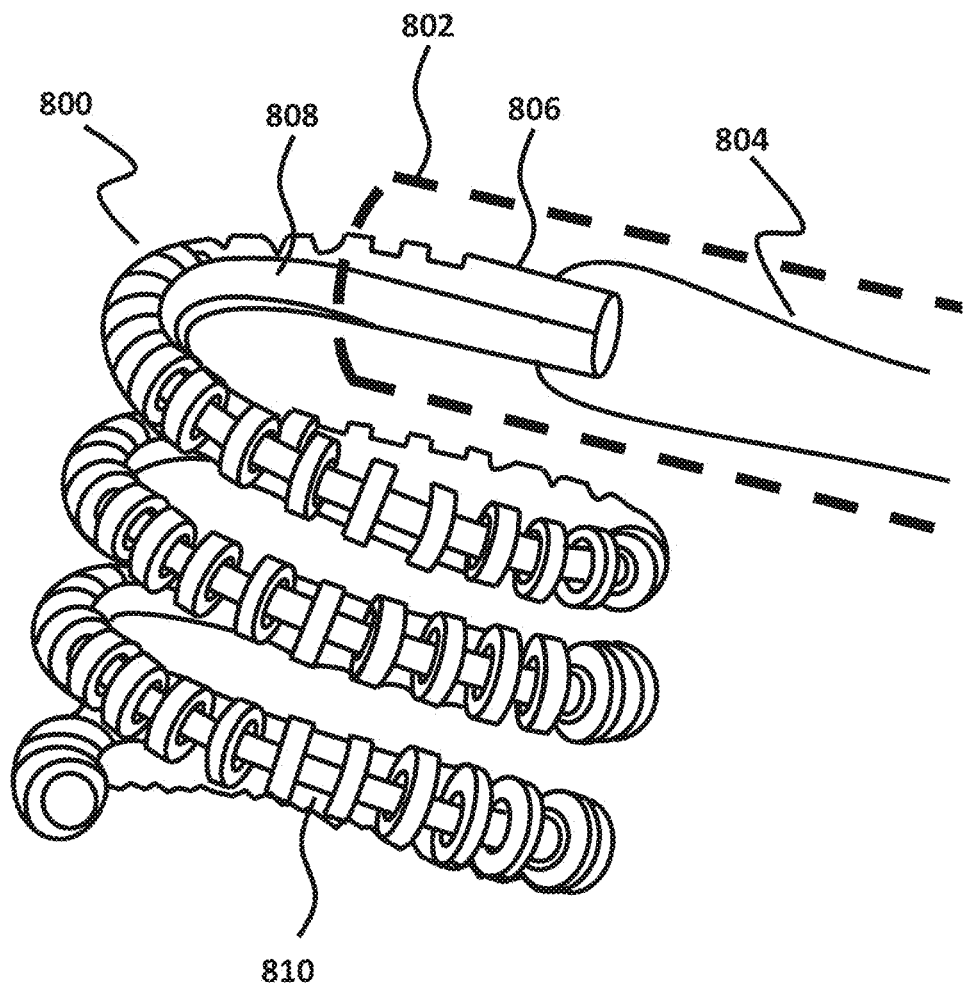
FIG. 8 illustrates an embodiment of an embolic device being loaded into an introducer with a suture threaded through a fenestration machined on a distal end of the embolic device.

FIG. 8 illustrates embolic device 800 being loaded into an introducer 802. A suture 804 is threaded through the proximal end 806 of embolic device 800, which allows the user to simply pull the suture backward to load the embolic device in the introducer 802. The suture 804 is threaded through a top fenestration 712 and a bottom fenestration 718 (forming an opening along the latitudinal axis of the tube structure) as illustrated in FIG. 7. The suture 804 may be removed after the length of the embolic device has been pulled into the introducer 802. The embolic device 800 may then be loaded into the proximal end of a delivery catheter with a supplied plunger device.

In particular, FIG. 8 illustrates yet another example of an embolic device with a continuous, uncut spine 808. When loading embolic device 800 into the introducer 802, the uncut spine 808 enables embolic device 800 to smoothly slide into the introducer 802. If the embolic device 800 were loaded into the introducer 802 with the uncut spine 808 facing the lip of introducer 802, the micro-machined fenestrations 810 would make it difficult to load the embolic device 800 into the introducer, as the micro-machined fenestrations 810 would get caught and ratchet against the lip of introducer 802 and against the inner walls of introducer 802.

When the embolic device is delivered to the site of therapy, it is also important for the smooth side of the embolic device to make contact with the lip of the catheter as the embolic device exits the catheter. Similar to the issue faced during loading of the embolic coil into the introducer, if the fenestrations slide against the lip of the catheter as the embolic device exits the catheter, the fenestrations can get stuck on the lip. In such cases, the use of a flexible and torqueable delivery device helps reorient the catheter to ensure that the side of the embolic device without any cuts makes contact with the lip of the catheter.

Figure 9:
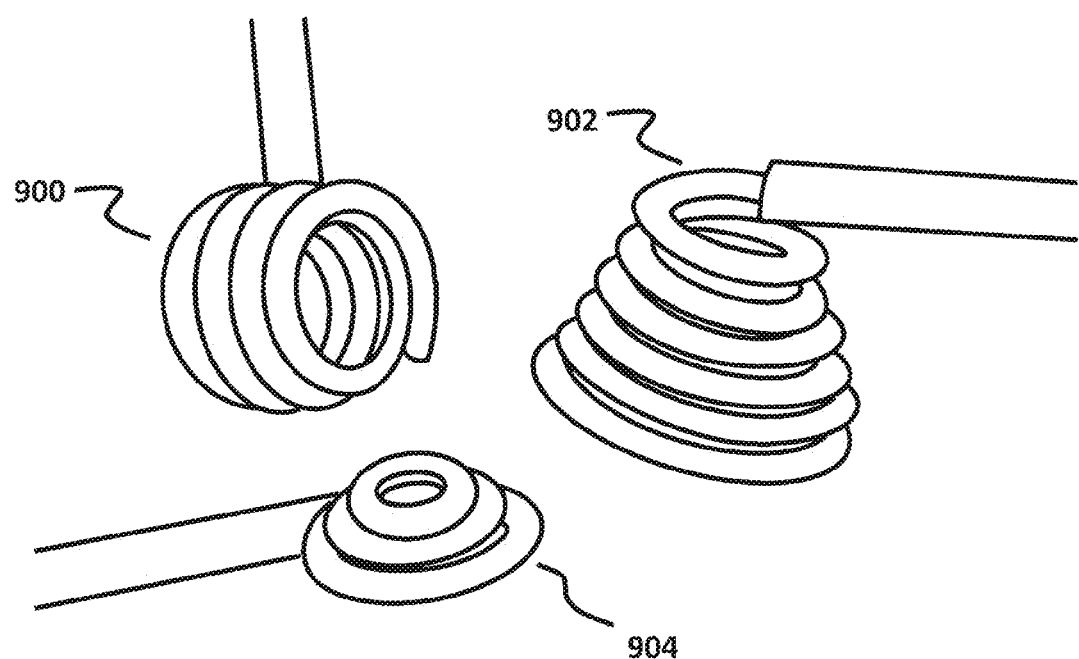
FIG. 9 illustrates three examples of spiral shapes of embolic devices in accordance with an embodiment.

FIG. 9 illustrates the shape of three embolic devices being loaded into introducers. As indicated above, the embolic coils may be micro-machined to assume any desired shape, size, length, etc. The first embolic device 900 has a substantially cylindrical shape. The second embolic device 902 and the third embolic device 904 have a substantially upward spiral shape. The embolic devices from FIG. 9 are merely examples of the plurality of shapes that may be created with the micro-fabricated fenestrations described herein. The embolic devices in FIG. 9 are illustrated without fenestrations for illustration purposes, as the goal was to illustrate shapes that may be assumed by embodiments of embolic devices.

Coils that are stretched may be used with embodiments of embolic devices described herein. Stretching the inner coil further increases the surface area that comes in contact with blood, and provides additional surface area where blood and other bodily fluids can enter and where tissue can grow. As noted above, the pitch of the inner coil may be varied over one or more portions of the embolic device. For instance, a first coil pitch may be used near the ends of the inner coil and a second coil pitch may be used throughout the rest of the inner coil. FIGS. 7A and 7B illustrate the coil pitch changing near the proximal end of the embolic device. Alternatively, one or more portions of the inner coil may alternate between a first coil pitch and a second coil pitch. If the first coil pitch is less than the second coil pitch, then the inner coil may slowly transition from a tightly wound coil to a more stretched coil. The transition of the coil pitch may also be almost immediate, with the first coil pitch changing to the second coil pitch from one loop of the coil to the next. The use of a variable coil pitch improves the transition from the inner coil to the tube of the embolic device.

Figure 10A:
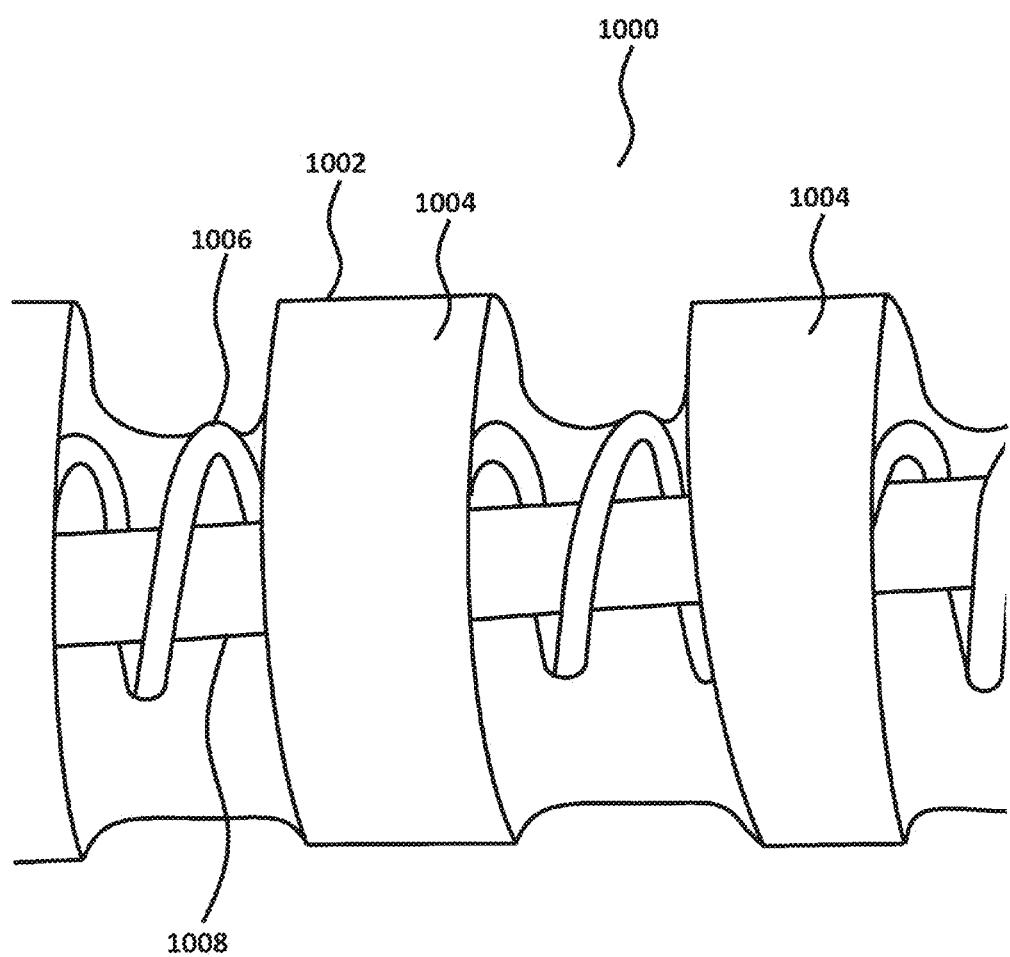
FIGS. 10A and 10B illustrate a top-down view and a side view of an embolic device with a fiber disposed within the inner coil in accordance with an embodiment.

FIG. 10A illustrates a top down view of a portion of an embolic device 1000. The embolic device 1000 includes a tube structure 1002 with various fenestrations, forming resultant beams (rings) 1004. The fenestrations expose the inside of tube 1002, including inner coil 1006 and a fiber 1008 on the inside of inner coil 1006. The inner coil 1006 has a high coil pitch (loosely wound), allowing access to the lumen of inner coil 1006 and access to fiber 1008. Fiber 1008 may be a glass fiber, a polymer fiber, a loadable fiber, or a micropore loadable fiber. Regardless of the type of fiber 1008, it may be loaded with an agent that delivers treatment to the delivery site.

The use of glass fibers has several advantages. The glass fiber on the inside of the inner coil increases the elastic modulus of the embolic device. This also gives more strength to the embolic device in the annealed position. The use of glass fibers also makes the embolic device more thrombogenic due to glass being a highly thrombogenic material. Consequently, the use of glass fibers on the inside of the embolic coil attracts blood to the lumen of the inner coil 1006, increasing the effectiveness of the embolic device to form a clot.

In particular, the hollow tubular structure of the embolic device provides a vehicle for delivery or simply passive response agents, such as glass fibers or more active agents. The interior of the embolic device may also be loaded with slow release materials that can provide additional features to chemotherapeutic delivery. This can include a timed release, or simply more of the agent being held within the embolic device. Complete or partial fenestration filling may be used to control agent release. For instance, the filling polymer used for altering the flex response of the tube can actually contain an agent that is slowly released when the embolic device is deployed to the delivery site. The inside of the inner coil may also be loaded with a radioactive fiber, with radioactive beads, or with embolic particles (further described below).

Figure 10B:
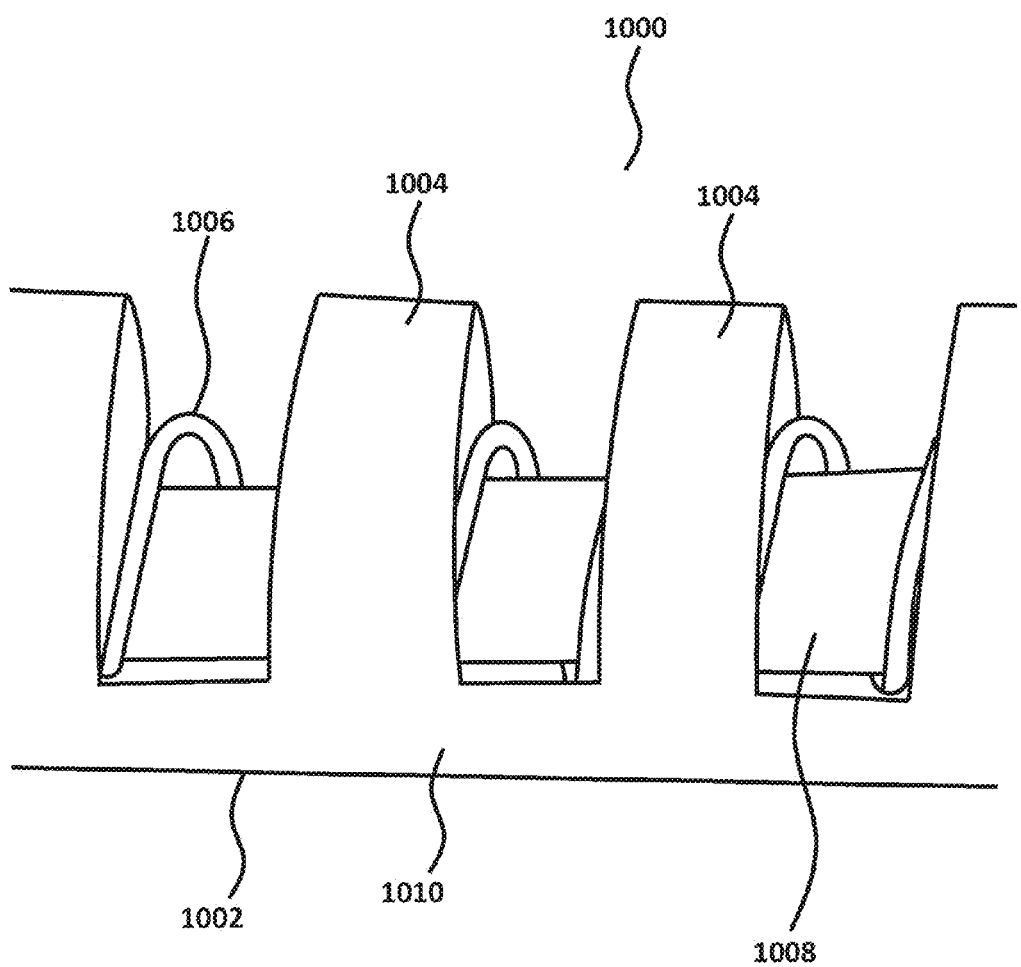

FIG. 10B illustrates a side view of a portion of embolic device 1000. FIG. 10 shows the tube 1002 having micro-machined fenestrations that resulting from cutting almost two thirds of the tube 1002, leaving only a thin, uncut spine along the bottom portion of the tube 1002. FIGS. 10A and 10B illustrate fenestrations that are uniform in size and shape, but as described above, the size and shape of fenestrations may be varied, and larger spacing windows may be used to control the shape assumed by the embolic device.

Figure 11A:
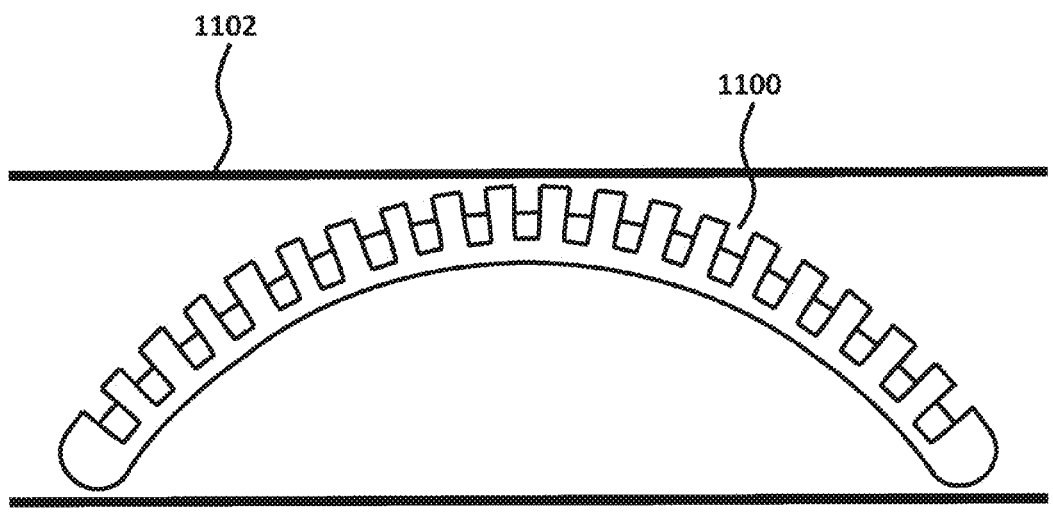
FIG. 11A illustrates an example of a banana shaped embolic device in accordance with an embodiment.

FIG. 11A illustrates an embodiment of an embolic device 1100 having a banana shape. The banana shaped embolic device includes the tube with micro-machined fenestrations along the top portion of the tube, with an uncut spine along the bottom of the tube, and an inner coil disposed within the tube. In particular, the embolic device is illustrated deployed within a vessel 1102. The banana shape enables the embolic device to anchor against the walls of the vessel 1102. When coils are inserted into the anatomy from a catheter, they almost always do not achieve the precise shape they are intended to form. This is true for detachable coils for aneurysms or other applications, pushable coils of all shapes, etc. This is also true for the subject coils, although they have other capabilities that control the "imperfect" deployment to a greater extent. In comparison with the folding embolic device described above, embolic device 1100 consists of uniform micro-machined fenestrations without larger spacing windows. In addition, because the embolic device consists of a simple and smooth curve, the embolic device is smaller than the embolic device that would be needed to form a folding and dense shape (as illustrated in FIG. 5).

If a coil is deployed from a catheter into an environment where it does not encounter anatomy or other constraint, it will form the intended shape that is set into the coil. In the anatomy, the coil almost always encounters a vessel wall early in the deployment. Once the elongate coil touches a wall or other constraint, the catheter and/or coil must move in order to allow the coil to recreate its intended shape. These movements are not always possible or desirable, and thus the coil forms a modified shape in the anatomy. Fortunately, these "new" shapes function sufficiently well for the relatively forgiving process of clot formation and occlusion. This condition can, however, lead to the need for additional coils, which the banana shaped embolic device 1100 can improve.

Figure 11B:
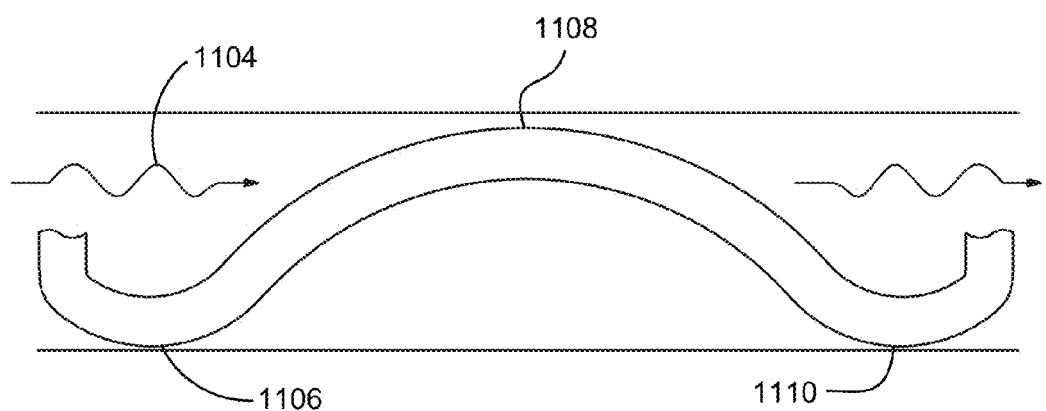
FIG. 11B illustrates an example of a banana shaped embolic device with flow tripping elements to generate turbulence in a flow in accordance with the present embodiment.

For longitudinal coils such as embolic device 1100, recreation of precise shape en-vivo is easier to achieve. In FIG. 11B, the end 1104 can have a 90 degree bend, which sits in centerline of the vessel and can easily move away from the vessel wall. Note the 90 degree angle segment could also advantageously be a very small "ball" or otherwise bunched coil segment. Upon deployment, the end 1104 and distal in-line curve 1106 may touch the vessel wall and be pulled slightly downstream, ensuring an elongate deployment. The center in-line curve 1108 may encounter the opposing vessel wall. The proximal in-line curve 1110 may then touch the other side of the vessel. Finally, the very proximal end 1112 having a 90 degree angle, bunched ball, or even no geometry would emerge and form. The result is a structure with several macro and micro flow trips for example, the proximal end, the micro flow trips along the coil, and/or the distal end. FIG. 11B does not depict the micro-fabricated fenestrations on the embodiment, however, it should be understood that FIG. 11B illustrates the general shape of an embodiment, which may then have any of the herein described fenestration or surfaces features disposed thereon to achieve any additional desired performance.

An advantage of this embodiment may include improved clotting based on flow dynamics. As described earlier, the various fenestrations may create a flow trip (i.e. a boundary layer that changes the fluid dynamics from a laminar flow to a turbulent flow). Tripping the blood flow may create eddy currents, stagnation, or other flow dynamics that may increase the effectiveness of the embolic coils.

Figure 12:
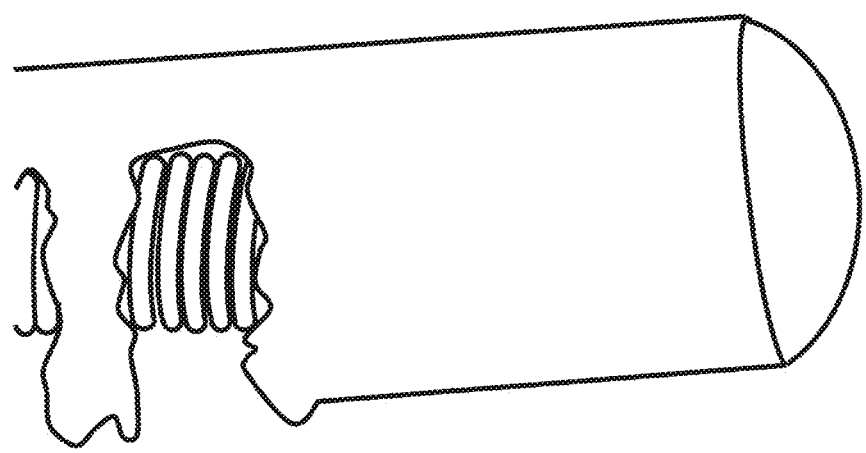
FIG. 12 illustrates an embodiment of an embolic device with the inner coil secured to the tube structure with UV glue balls on the ends of the embolic device.
Figure 13:
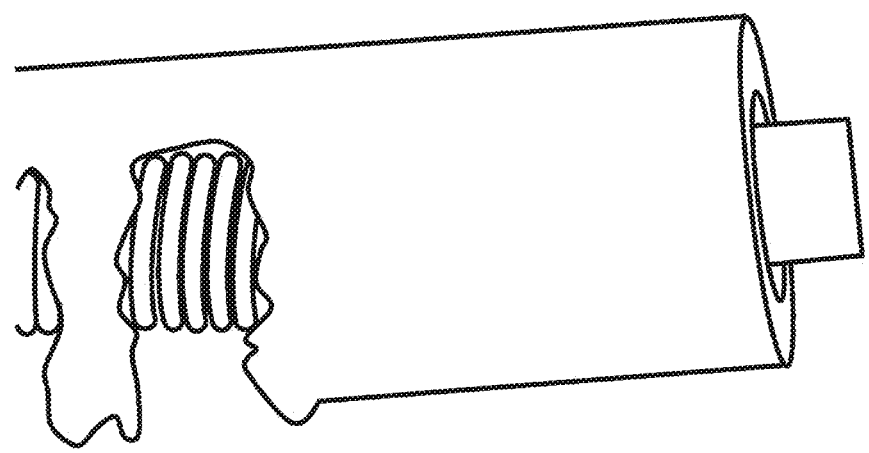
FIG. 13 illustrates an embodiment of an embolic device with the inner coil secured to the tube structure with a PEEK rod inserted and melted into the ends of the embolic device.

In embodiments described herein, the inner coil may be secured to the sleeve of the embolic coil using various methods. FIG. 12 illustrates an embodiment of an embolic coil with the ends of the embolic coil secured with a UV glue ball. In yet another embodiment, in the ends of the embolic coil, the PEEK sleeve may be melted, forming a rounded end that secures the inner coil within the sleeve. FIG. 13 illustrates an embodiment where a PEEK rod was inserted into the end of the embolic coil in order to melt the two together. This may be performed in addition or as an alternative to the melting of the ends of the PEEK sleeve. In further embodiments, an embolic coil may be formed as described herein, but one or more of the ends of the embolic coil may be left open and/or the inner coil may remain unsecured. For example, the sleeve may be a nitinol sleeve that is biased toward its deployed state to limit longitudinal movement of the inner coil. In other embodiments, the sleeve may be another polymer that is biased toward its deployed state.

In one embodiment, a steel wire mandrel may be inserted along the length of the embolic device. The steel wire mandrel may be inserted into the lumen of the inner coil, or it may be inserted between the inner wall of the tube structure and the outer surface of the inner coil. The steel wire mandrel provides structural support for enabling the ends of the tube structure to be crimped or tapered with heat. For instance, the ends of the PEEK tube structure may be heated, and inserted into a cone shaped element that forces the heated PEEK to crimp. The ends of the PEEK tube being crimped (or reduced in size because of being tapered), secures the inner coil within the PEEK tube without an adhesive. For example, if the inner coil has a diameter of 30 thousandths of an inch, and the PEEK tube has a diameter of 33 thousandths of an inch, then squishing the ends of the PEEK tube to a diameter of less than or equal to 30 thousandths of an inch would secure the inner coil within the PEEK tube. For a particular application, such as in peripheral vasculature or in an aneurysm, different outer diameters for the coils may be used. An example outer diameter for the coils would be about 33 thousandths of an inch. In another application, an example outer diameter of the coils would be about 25 thousandths of an inch. In yet another application, an example outer diameter would be about 18 thousandths of an inch. In some embodiments, the outer diameter of the coil may be between about 12 thousandths of an inch and about 38 thousandths of an inch.

Yet another embodiment of the present disclosure is directed to a method of sealing off a particle bed. The use of radio therapy through radioactive embolic microspheres for Hepatocellular carcinoma (HCC) is gaining in prevalence. In conjunction with this therapy, embolic devices as described herein may be used to follow up or seal off the particle bed. For example, small feeder embolic devices may be used to seal feeder vessels without actually coiling in the artery. The feeder coils may also be made less thrombogenic (such as by coating the tube with a hemocompatible material) and retrievable, adding therapy options. A radiotherapy material can also loaded into the interior of an embolic device, such as by including a fiber loaded with a radio-theurapeutic agent or by including a radioactive fiber. The inside of the embolic device may also be loaded with radioactive beads.

Particle treatment, such as using microspheres, beads, or particles having other shapes, is different from coils. Particle treatment may be used in conjunction with or independently of embolic coils. Embolic particles are typically about 50 microns (about 2 thousandths of an inch) to about 300 microns (12 thousandths of an inch) along a major axis. They are used to arrest blood flow to the cell, very close to the cell. They may be large enough to not pass through the capillary bed into the venous system and on to the lungs, heart, and rest of body. Shutting down flow close to the cell will reduce collateralization supply effect to the cell, which may affect the need or applicability of embolic coil treatment. Particles are less effective at treating trauma or aneurysm. Embolic particles may be delivered in suspension, and the suspension injected at or near the desired therapeutic site rather than pushed into position using a delivery mechanism, such as a catheter.

In an embodiment, surface treatments may be used to enhance surface area and/or surface activity of an embolic device. In some embodiments, bead-blasting may be applied either before or after the tube of the embolic device is micro-machined with fenestrations. In other embodiments, abrasive blasting techniques may also be used to enhance the surface area of the tube. Abrasive blasting techniques may also be used for the treatment of embolic particles described below. Finally, the PEEK tube lends itself better to the application of drug delivery coatings (to further control delivery rates and mechanical properties) than metal coils. The PEEK tube may also be treated with a lubricious coating to reduce dynamic friction. A tie layer may be added to the embolic device to include a fibrinogen agent.

Figure 14:
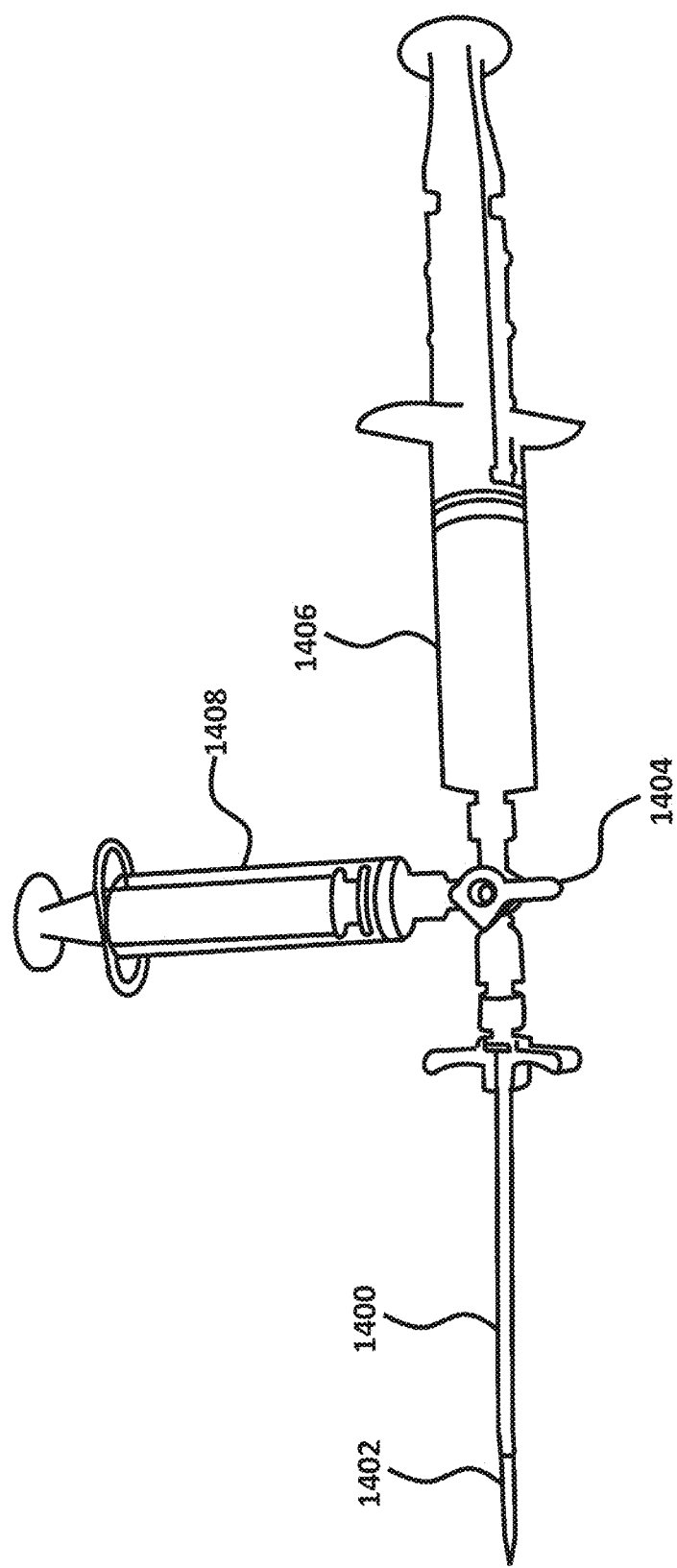
FIG. 14 illustrates an aspiration prep method for loading an embolic device with an agent or bodily fluids.

A loadable fiber may be loaded with an agent in an introducer using aspiration preparation. FIG. 14 illustrates aspiration preparation being used to load an embolic device or embolic particles with an agent or bodily fluids. An embolic device (not illustrated) is placed inside of introducer 1400. The introducer 1400 includes a first stopcock 1402 and a second stopcock 1404. The first stopcock 1402 seals a first end of the introducer. However, in other embodiments, an introducer with one of the ends sealed may also be used for the aspiration preparation method described herein. The second stopcock 1404 seals the second end of the introducer, but throughout the aspiration preparation, the second stopcock is opened to create a vacuum in the introducer 1400 and to fill the introducer 1400 with an agent or bodily fluid.

Two syringes are connected to the second stopcock 1404, vacuum syringe 1406 and an agent syringe 1408. The vacuum syringe 1406 is used to create a vacuum in the introducer 1400 in order to pull the air out of the introducer 1400. The agent syringe 1408 is used to pump an agent or bodily fluid intro the introducer 1400. The second stopcock 1404 is used to which of the vacuum syringe 1406 and agent syringe 1408 is open (only one is open at any one time).

During aspiration preparation, the second stopcock 1404 may be turned to open the vacuum syringe 1406 and to close the agent syringe 1408. The vacuum syringe 1406 may be used to pull the air out of the introducer 1400 by pulling the plunger of vacuum syringe 1406. The vacuum created in the introducer 1400 may result in any air bubbles remaining in the introducer 1400 expanding to a very large size. The second stopcock 1404 may then be turned to close the vacuum syringe 1406 and to open the agent syringe 1408. The agent syringe 1408 may contain an agent for loading the embolic device and any fibers loaded inside the embolic device. The plunger of the agent syringe 1408 is pushed in order to load the introducer with the agent. The second stopcock 1404 may then be turned to close agent syringe 1408 and open the vacuum syringe 1406, and the process may be repeated until no more agent may be loaded into introducer 1400. This process may enable substantially all of the spaces containing air in the fibers and in the embolic device to be loaded with the desired agent.

The aspiration preparation can thus be used to load the embolic device and/or embolic particles to with a fibrinogen agent, a therapeutic agent, a radiotherapy agent, a chemotherapeutic agent, etc. The fiber can also include a drug delivery coating to control the delivery rates of drugs to the treatment site. Rather than using an agent, aspiration preparation may be used to load embolic devices and embolic particles with autologous blood (or other bodily fluid). The embolic device or embolic particles may be inserted into introducer 1400 and the aspiration preparation method described above performed.

Figure 15:
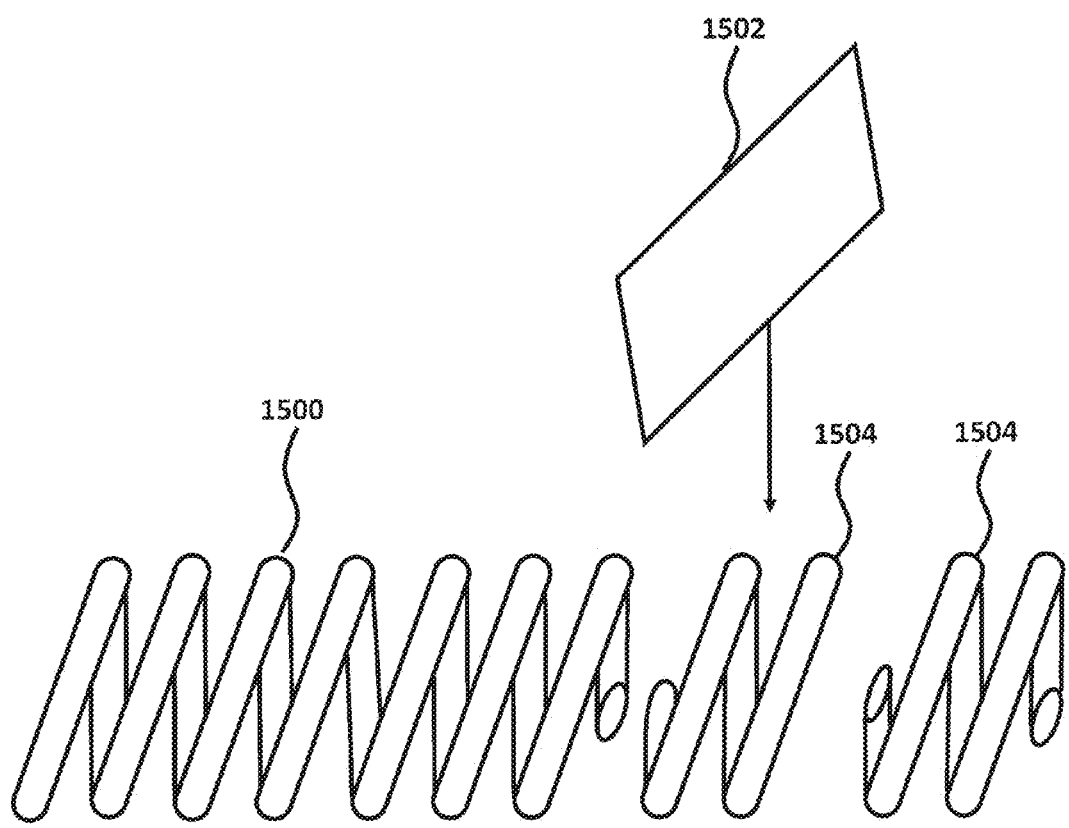
FIG. 15 illustrates embodiments of embolic particles micro-cut from an embolic device.

Yet another embodiment is micro-fabricated embolic particles, with micro-cuts formed on the surface of embolic particles in order to create embolic particles with an irregular surface that increases the surface area that comes in contact with tissue and bodily fluids. FIG. 15 illustrates a method of micro-fabricating embolic particles by micro-cutting an embolic device as described in reference to FIGS. 1-13. For illustration purposes, embolic device 1500 is presented without fenestrations and without the inner coil. However, it is to be understood that embolic device 1500 is comprised of a micro-fabricated tube structure with fenestrations and an inner coil disposed within the tube structure.

In FIG. 15, the embolic device 1500 has a substantially cylindrical shape in order to facilitate the micro-cutting process. Specifically, embolic device 1500 is micro-cut with a blade 1502 to create embolic particles 1504. The embolic particles 1504 are shown as consisting primarily of two loops of coiled shape of embolic device 1500. However, the embolic particles 1504 need not be uniform, and they may consist of a single loop of the coiled shape of embolic device 1500, or consist of at least two loops. For instance, the micro-cutting machine used to create the embolic particles may be programmed to create embolic particles that are all substantially the same size and shape. Alternatively, the micro-cutting machine may be programmed to create embolic particles of varying sizes. Finally, while FIG. 15 illustrates the use of a blade of a micro-cutting machine, alternative embodiments may use other techniques and tools (such as laser cutting) to create the embolic particles 1504 from the embolic device 1500.

In embodiments where the embolic device consists of a PEEK tube structure and a tantalum inner coil, the resulting embolic particles will similarly consist of a PEEK tube structure and a tantalum inner coil. The embolic particles may also consist of less than one loop, resulting in embolic particles whose size is less than one loop, such as half a loop, a quarter of a loop, etc. The micro-cutting of embolic device that is tightly coiled vs. loosely coiled, also enables the micro-fabrication of embolic particles of varying size without having to reprogram the micro-cutting of blade 1502.

FIG. 16 illustrates different embodiments of embolic particles. The embolic particles illustrated in FIG. 16 have a substantially cylindrical shape. FIG. 16A illustrates a front view of an embolic particle 1600. Embodiments of embolic particle 1600 may optionally include a machined lumen 1602. The lumen 1602 increases the surface area of the embolic particle 1600 that comes in contact with bodily fluids and tissue. The lumen 1602 also enables a wire to be threaded through the particles, facilitating controlled delivery of embolic particles to the treatment site. Finally, the lumen of embolic particles may be loaded with an agent or with a loadable fiber in order to deliver treatment to the treatment site. FIG. 16B illustrates a side view of embolic particle 1600, with the dashed lines indicating the lumen 1602. FIG. 16C illustrates the embolic particle 1600 with top section 1604 and bottom section 1606 of the front face 1608 and the back face 1610 cut at an angle. The top section 1604 and bottom section 1606 may be cut at any angle between about 0 degrees and 180 degrees.

Figure 16A:
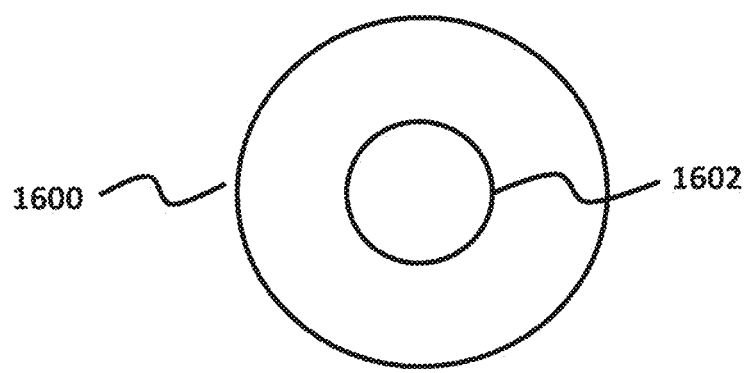
FIGS. 16A-F illustrate various embodiments of micro-machined embolic particles.
Figure 16B:
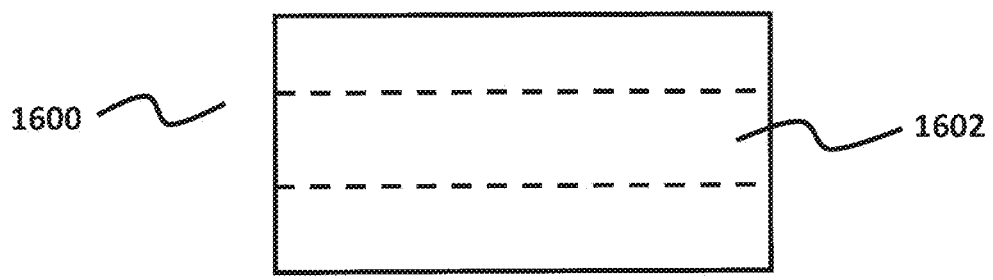
Figure 16C:
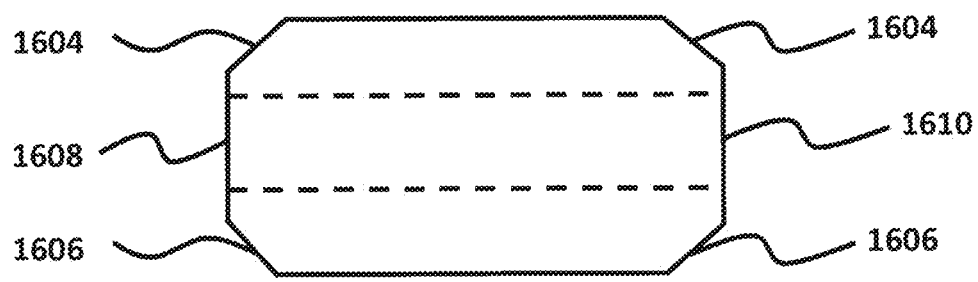
Figure 16D:
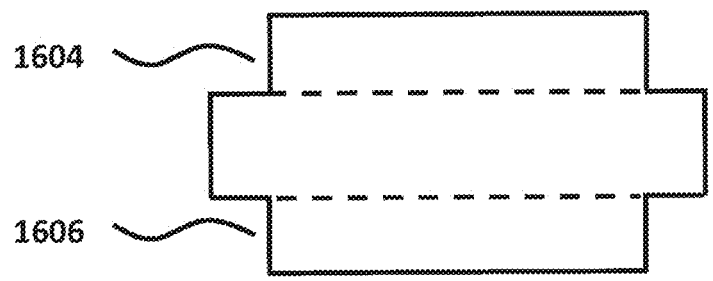
Figure 16E:
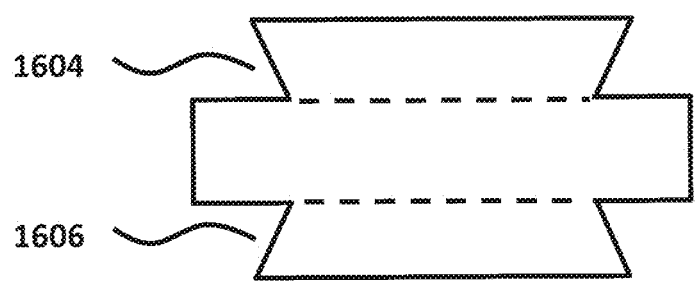
Figure 16F:
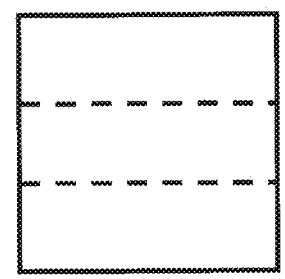

FIG. 16D illustrates an example embolic particle with the top section 1604 and the bottom section 1606 cut at a 90 degree angle. FIG. 16E illustrates yet another example of an embolic particle with the top section 1604 and the bottom section 1606 cut at an over 90 degree angle. The cutting of the faces of the embolic particle increases the surface area of the embolic particle, thus increasing the effectiveness of forming a clot. Finally, FIG. 16F illustrates an example of a substantially cube shaped embolic particle vs. the elongated prism- or cylinder-shaped embolic particles from FIGS. 16A-16E.

Embolic particles can have the top section 1604 cut differently than the bottom section 1606. For example, the top section 1604 may be cut at a first angle, while the bottom section 1606 may be cut at a second angle. The top section 1604 may be cut, with the bottom section 1606 left uncut, or vice versa. The front face 1608 and the back face 1610 of the embolic particle may also be cut differently. For instance, the front face 1608 may be cut as illustrated in FIG. 16D, and the back face 1610 may be cut as illustrated in FIG. 16E. In addition, the front face 1608 may be cut, while the back face 1610 may be uncut, or vice-versa. It is also to be understood that a set of embolic particles delivered to a specific site may be uniform, or they can consist of varied cutting patterns and shapes. In addition, while embodiments of embolic particles disclosed herein are illustrated having a lumen, alternative embodiments can consist of embolic particles without a lumen.

Figure 17A:
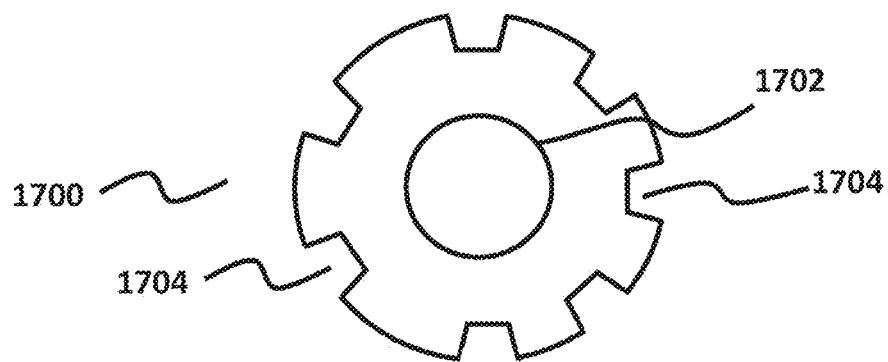
FIGS. 17A-C illustrate the micro-machining of an irregular surface on embolic particles.

FIG. 17A illustrates a front view of an embodiment of an embolic particle with a micro-machined surface. Embolic particle 1700 includes a lumen 1702, and micro-machined cuts 1704 on the outer surface of the embolic particle 1700. The micro-machined cuts 1704 may be uniform around the outer surface of the embolic particle 1700. Alternatively, the micro-machined cuts may be made randomly so as to create a rough exterior surface on the embolic particle increasing the surface area that comes in contact with tissue and bodily fluids. The micro-machined cuts can vary in terms of length, depth, and the cutting angle. The cuts may be uniformly spaced, or they may be randomly spaced. As noted above, any of the embolic particles described herein may or may not include a lumen.

Figure 17B:
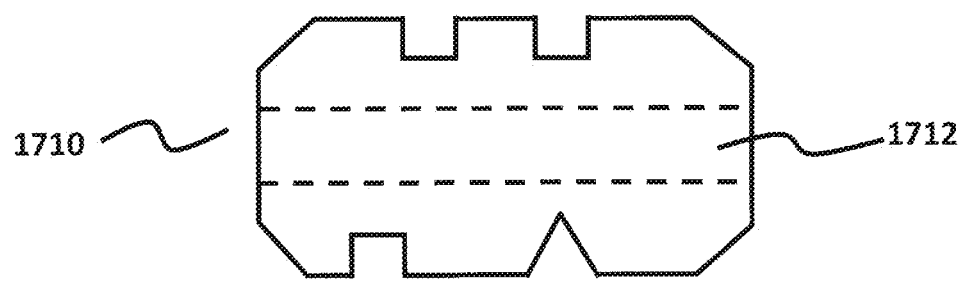
Figure 17C:
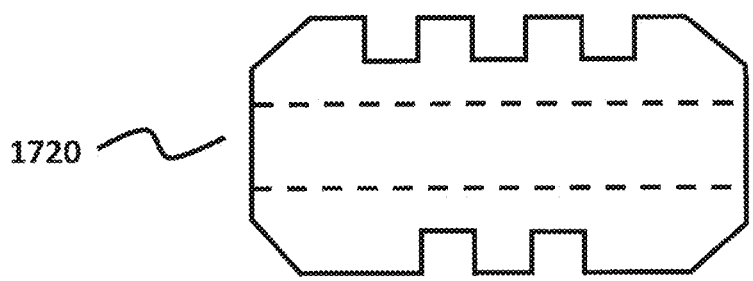

FIG. 17B illustrates a side view of an embolic particle 1710, with the dashed lines representing lumen 1712. In particular, embolic particle 1710 includes two uniform micro-machined cuts along the top of the embolic particle 1710 and two non-uniform micro-machined cuts along the bottom of the embolic particle 1710. The two cuts on the bottom of the embolic particle differ in depth and in the cutting angle, with the first resulting cut being substantially rectangular and the second resulting cut being substantially triangular. FIG. 17C illustrates yet another example of an embolic particle 1720, having three uniform micro-machined cuts along the top surface of the embolic particle, and having two uniform micro-machined cuts along the bottom surface of the embolic particle. It is to be understood that the cutting techniques described above used for the micro-machining of embolic devices may also be used for embodiments of embolic particles. For example, embolic particles may be micro-machined by having simultaneous cuts formed along the top and bottom of the embolic particles. Alternatively, an embolic particle may be micro-machined with cuts along either the top or the bottom portion, resulting in the embolic particles having a continuous uncut spine (or continuous uncut side). The micro-machined cuts of the embolic particle can also rotate around the circumference of the embolic particle and along the length of the particle.

In some embodiments, embolic particles may be made by processing a thin film or a thick film. Such thin film or thick film processing may be similar to methods used in microelectronics or microelectronic production (MEMS). Using thin films may allow for very fine particles to be made with micro- or even nano-scale features. As used herein, "microscale" means 1 micron or greater and less than 1 millimeter while "nano-scale" means 1 nanometer or greater and less than 1 micron. These fine particles, whether including micro- or nano-scale features or not, may be biologically interactive due to size. The fine particles also may have mechanical features such as surface features or pores that hold agents such as chemotherapy agents or agents to promote thrombogenicity. The surface feature or pores may be configured to hold fluid via surface tension or capillary forces.

In thick film methods, a silk screen type "mask" may be used to deposit material on to a substrate in an ordered array. In such a case, the deposited material or "ink" could be made of various materials, including metals. After the silk screen application or applications (for multiple layers and 3-D features, including altering material content) the substrate is sintered to drive off delivery solvents and fluids, and to form the mechanical properties in the resultant embolic (metal or other particle).

Forming the micro- or nano-scale embolic particles on thick film in an ordered array allows for improved methods of locating the individual pieces and loading them onto a wire. Micro-electronics assembly techniques are well established for indexing a substrate and locating micro-scale features on the substrate (such as a silicon wafer or printed circuit board). Intricately designed particles with holes for stringing (or no holes in alternative embodiment and delivery methods) can be formed and then strung on a wire using automation.

FIG. 18 illustrates three types of delivery methods for embolic particles described herein. FIG. 18 presents four embolic particles for illustration purposes. However, it is to be understood that hundreds and/or thousands of embolic particles may be delivered using the methods described herein.

Figure 18A:
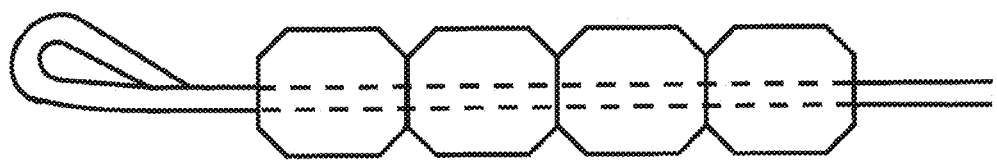
FIG. 18A-C illustrate three methods for delivering embolic particles with a high degree of control.

FIG. 18A illustrates the use of a core wire that is threaded through the lumen of the embolic particles, thus stringing the embolic particles together for delivery. In particular, FIG. 18A illustrates the end of the core wire twisted to keep the particles from slipping off the end of the core wire. Specifically, the core wire is twisted to form a loop slightly larger than the lumen of the embolic particles. The core wire is flexible enough to be pulled back, such that the pulling of the wire untwists the end of the core wire as it is forced to fit through the lumen of the leading embolic particle. As the wire untwists and pulled back, the embolic particles may be delivered in a controlled fashion. For instance, a nitinol core wire is flexible to enable the end of the nitinol wire to be folded and enabling the core wire end to be untwisted by pulling the core wire back.

Figure 18B:
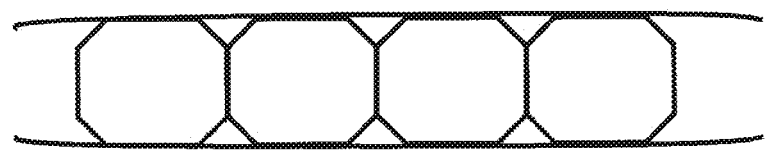

FIG. 18B illustrates the use of a tight fitting sleeve to deliver embolic particles. The irregular outer surface of the embolic particles would enable the embolic particles, in addition to a tight fitting sleeve, to secure the embolic particles during delivery. The sleeve may be soft, but not stretchable; otherwise it would not be possible to push the embolic particles out of the sleeve. Alternatively the particles could be injected, using the sleeve as a valve, which opens somewhat to allow for particle release.

Figure 18C:
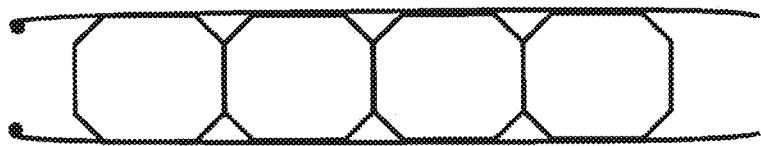

FIG. 18C illustrates the use of a sleeve with an occlusion cuff or an interference fit to deliver embolic particles. The occlusion cuff or the interference fit prevents the embolic particles from being dispersed until sufficient pressure is applied to push the embolic particles past the interference fit or occlusion cuff. In the embodiments illustrated in FIGS. 18A-18C, the embolic particles may be delivered through a catheter, further facilitating controlled delivery to the treatment site.

An embodiment is directed to an embolic device designer. In an embodiment, a user can browse through a selection of embolic device shapes, with the selection of one of these shapes communicating to a micro-cutting machine the necessary instructions for micro-cutting the embolic device. The micro-cutting machine may be used for machining catheters, guidewires, embolic devices, embolic particles, and other devices. For example, the micro-cutting machine as described in U.S. patent application Ser. No. 12/633,727, which is incorporated herein by reference, may be used to micro-machine embolic devices. The programming provided by the controllers of the micro-cutting machine may be used to provide extremely precise computer controlled movement of the micro-cutting machine. For example, the rotational motor of the micro-cutting machine may be programmed to rotate the embolic device a number of degrees, and feed the embolic device through the machine so that blades can micro-cut the necessary fenestrations. Additional aspects of the micro-cutting machine that may be programmed include the position of the blades to make cuts resulting in the desired resultant beam width, the use of a single blade, the use of two blades to make opposite cuts on the embolic coil, and the spacing windows, etc.

The methodologies described herein may be implemented by various means depending upon applications according to particular examples. For example, programmed control of micro-cutting machines may be implemented in hardware, firmware, software, or combinations thereof. In a hardware implementation, for example, a processing unit may be implemented within one or more application specific integrated circuits ("ASICs"), digital signal processors ("DSPs"), digital signal processing devices ("DSPDs"), programmable logic devices ("PLDs"), field programmable gate arrays ("FPGAs"), processors, controllers, micro-controllers, microprocessors, electronic devices, other devices units designed to perform the functions described herein, or combinations thereof.

Some portions of the detailed description included herein are presented in terms of algorithms or symbolic representations of operations on binary digital signals stored within a memory of a specific apparatus or special purpose computing device or platform. In the context of this particular specification, the term specific apparatus or the like includes a general purpose computer once it is programmed to perform particular operations pursuant to instructions from program software. Algorithmic descriptions or symbolic representations are examples of techniques used by those of ordinary skill in the signal processing or related arts to convey the substance of their work to others skilled in the art. An algorithm is herein, and generally, considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals, or the like. It should be understood, however, that all of these or similar terms are to be associated with appropriate physical quantities and are merely convenient labels. Unless specifically stated otherwise, as apparent from the discussion herein, it is appreciated that throughout this specification discussions utilizing terms such as "processing," "computing," "calculating," "determining" or the like refer to actions or processes of a specific apparatus, such as a special purpose computer or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device.

Reference throughout this specification to "one example," "an example," and/or "another example" should be considered to mean that the particular features, structures, or characteristics may be combined in one or more examples. The terms "approximately," "about," and "substantially" as used herein represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of a stated amount.

While there has been illustrated and described what are presently considered to be example features, it will be understood by those skilled in the art that various other modifications may be made, and equivalents may be substituted, without departing from the disclosed subject matter. Additionally, many modifications may be made to adapt a particular situation to the teachings of the disclosed subject matter without departing from the central concept described herein. Therefore, it is intended that the disclosed subject matter not be limited to the particular examples disclosed.

I claim:

1. An embolic device, comprising:
   a micro-fabricated tube having an outer surface and an interior surface forming a lumen extending from a proximal end to a distal end, the tube made of a first material and having a plurality of micro-fabricated fenestrations formed therein, the plurality of micro-fabricated fenestrations being aligned along a single side of the tube leaving a continuous, uncut spine opposite the fenestrations;
   an outer elastomer laminate layer in contact with at least a portion of an outer surface of the tube and partially filling one or more of the micro-fabricated fenestrations; and an inner coil made of a second material and disposed within the tube, the inner coil being secured to the tube, the one or more micro-fabricated fenestrations exposing the inner coil.

2. The embolic device as recited in claim 1, wherein the first material is polyetheretherketone (PEEK).

3. The embolic device as recited in claim 1, wherein the second material is tantalum.

4. The embolic device as recited in claim 1, further comprising a fiber disposed within the inner coil and the fiber is loaded with an agent.

5. The embolic device of claim 1, wherein the fenestrations are disposed along the micro-fabricated tube such that the micro-fabricated tube is configured to form a bend when in a deployed state so as to provide a flow trip when the embolic device is disposed in a moving fluid.

6. An embolic device, the embolic device comprising:
a first micro-fabricated body having a first length, first width and first height, the body having an outer surface and a first inner lumen extending from a proximal end to a distal end;
a plurality of micro-fabricated cuts formed in the outer surface of the first micro-fabricated body, the plurality of micro-fabricated cuts being aligned along a single side of the first micro-fabricated body to form a continuous, uncut spine opposite the cuts;
a first inner coil disposed within the first inner lumen and secured to the first micro-fabricated body;
a second micro-fabricated body having a second length, second width, and second height, the second body having an outer surface and a second inner lumen extending from a proximal end to a distal end;
a plurality of micro-fabricated cuts formed in the outer surface of the second micro-fabricated body, the plurality of micro-fabricated cuts being aligned along a single side of the first micro-fabricated body to form a continuous, uncut spine opposite the cuts;
a second inner coil disposed within the second inner lumen and secured to the second micro-fabricated body;
a delivery mechanism configured to deploy at least the first micro-fabricated body and second micro-fabricated body; and
a core wire disposed through the first inner lumen and the second inner lumen.

7. The embolic device as recited in claim 6, wherein the first micro-fabricated body comprises polyetheretherketone (PEEK).

8. The embolic device as recited in claim 6, wherein the first length, first width, and first height are substantially the same as the second length, second width, and second height.

9. An embolic device, comprising:
a micro-fabricated tube having an outer surface and an interior surface forming a lumen extending from a proximal end to a distal end, the tube made of a first material and having a plurality of micro-fabricated fenestrations formed therein, the tube also having one or more spacing windows disposed between successive sets of fenestrations, the one or more spacing windows being larger than the fenestrations to provide for folding of the embolic device at the one or more spacing windows; and
an inner coil made of a second material and disposed within the tube, the one or more micro-fabricated fenestrations exposing the inner coil.

10. The embolic device of claim 9, wherein the inner coil is secured to the tube.

11. The embolic device of claim 10, wherein the inner coil is secured to the tube at a first endpoint of the tube and at a second endpoint of the tube.

12. The embolic device of claim 10, wherein the plurality of micro-fabricated fenestrations are aligned along a single side of the tube to form a continuous, uncut spine opposite the fenestrations.

13. The embolic device of claim 9, further comprising an outer elastomer laminate layer disposed over at least a portion of the tube and partially filling one or more of the micro-fabricated fenestrations.

14. The embolic device of claim 9, wherein the first material is polyetheretherketone (PEEK).

15. The embolic device of claim 9, wherein the plurality of fenestrations rotate about the circumference of the tube with an angular offset between each successive fenestration or set of fenestrations.

* * * * *